United States Patent
Zhang et al.

(10) Patent No.: US 11,286,239 B2
(45) Date of Patent: Mar. 29, 2022

(54) ANGIOTENSIN II RECEPTOR 2 ANTAGONIST SALT FORM AND CRYSTALLINE FORM, AND PREPARATION METHOD THEREFOR

(71) Applicant: SHANDONG DANHONG PHARMACEUTICAL CO., LTD., Heze (CN)

(72) Inventors: Yang Zhang, Shanghai (CN); Wentao Wu, Shanghai (CN); Zhixiang Li, Shanghai (CN)

(*) Notice: Subject to any disclaimer, the term of this patent is extended or adjusted under 35 U.S.C. 154(b) by 0 days.

(21) Appl. No.: 17/179,382

(22) Filed: Feb. 18, 2021

(65) Prior Publication Data

US 2021/0206724 A1 Jul. 8, 2021

Related U.S. Application Data

(63) Continuation of application No. PCT/CN2019/115149, filed on Nov. 1, 2019.

(30) Foreign Application Priority Data

Nov. 2, 2018 (CN) .......................... 201811301892.3

(51) Int. Cl.
  *C07D 215/48* (2006.01)
(52) U.S. Cl.
  CPC ........ *C07D 215/48* (2013.01); *C07B 2200/13* (2013.01)
(58) Field of Classification Search
  CPC .................................................. C07D 215/48
  See application file for complete search history.

(56) References Cited

U.S. PATENT DOCUMENTS

| 9,095,587 B2 | 8/2015 | McCarthy et al. |
| 11,021,445 B2 * | 6/2021 | Zhang .................. C07D 401/12 |
| 2020/0102275 A1 | 4/2020 | Zhang et al. |

FOREIGN PATENT DOCUMENTS

WO 2018224037 A1 12/2018

OTHER PUBLICATIONS

Internatinal Search Report and written opinion of PCT/CN2019/115149, dated Feb. 20, 2020.
First Office Action for Australian Application No. 2019373178 dated Sep. 6, 2021.
Extended European Search Report for Application No. 198780165 dated Jul. 29, 2021.

* cited by examiner

*Primary Examiner* — D Margaret M Seaman
(74) *Attorney, Agent, or Firm* — W&KIP

(57) ABSTRACT

Disclosed are an angiotensin II receptor 2 ($AT_2R$) antagonist salt form and crystalline form, a preparation method therefor, and an application of the salt form and crystalline form in preparing a drug which treats chronic pain.

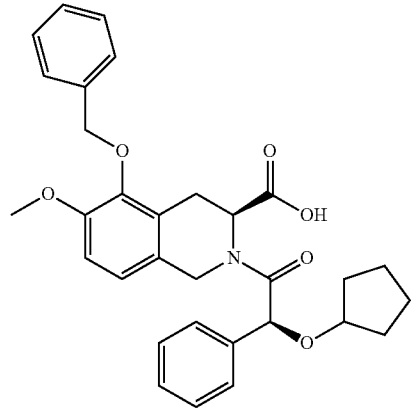

(I)

22 Claims, 7 Drawing Sheets

ANGIOTENSIN II RECEPTOR 2 ANTAGONIST SALT FORM AND CRYSTALLINE FORM, AND PREPARATION METHOD THEREFOR

CROSS-REFERENCE TO RELATED APPLICATION

This application is a continuation of International Application No. PCT/CN2019/115149, filed on Nov. 1, 2019, which claims priority to Chinese Patent Application No. 201811301892.3, filed on Nov. 2, 2018. All of the aforementioned patent applications are hereby incorporated by reference in their entireties.

TECHNICAL FIELD

The present disclosure relates to angiotensin II receptor 2 ($AT_2R$) antagonist salt form and crystalline form, and preparation method therefor, and also relates to use of the salt form and crystalline form in the preparation of drugs for treating chronic pain.

BACKGROUND

Angiotensin II (AngII) is an octapeptide produced by the hydrolysis of angiotensin I under the action of angiotensin converting enzyme, and has the functions of regulating blood pressure, body fluid balance and pain perception. Angiotensin receptors are G protein-coupled receptors with angiotensin as a ligand, and are an important part of the renin-angiotensin system. AngII can activate angiotensin II receptor 1 ($AT_1R$) and angiotensin II receptor 2 ($AT_2R$). $AT_2R$ is related to the mechanism of pain in the nervous system, and is mainly expressed in the dorsal root ganglia and trigeminal ganglia. $AT_2R$ is more highly expressed in damaged nerves and painful neuromas than in normal nerves. After $AT_2R$ is activated, the second messenger pathway activated by G protein-coupled receptors can sensitize ion channels in neurons. Sensitization results in the activation of ion channels to excite neurons. Through animal experiments and clinical experiments it has been proven that $AT_2R$ antagonists can be used to relieve pain.

WO 2011088504 (U.S. Pat. No. 9,095,587) discloses the compound EMA-401.

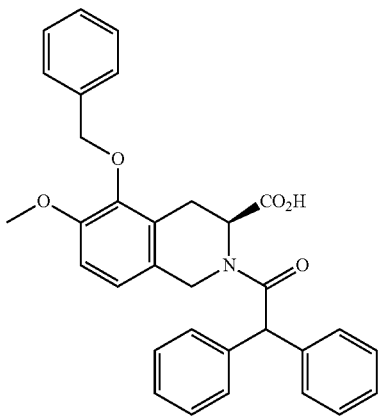

EMA-401

SUMMARY OF THE INVENTION

The present disclosure provides a compound represented by formula (I),

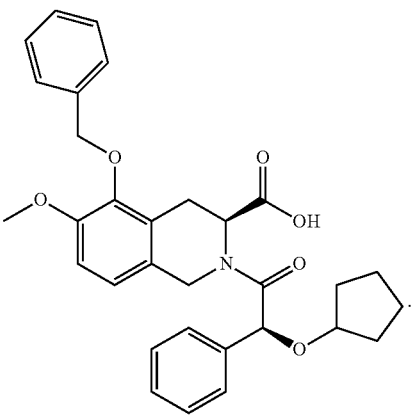

(I)

The present disclosure also provides a crystalline form "A" of the compound represented by formula (I), wherein an X-ray powder diffraction pattern of the crystalline form "A" has characteristic diffraction peaks at the following 2θ angles: 3.52±0.20°, 6.04±0.20°, and 18.21±0.20°.

In some embodiments of the present disclosure, the X-ray powder diffraction pattern of the crystalline form "A" has characteristic diffraction peaks at the following 2θ angles: 3.52±0.20°, 6.04±0.20°, 14.40±0.20°, 15.11±0.20°, 18.21±0.20°, 18.46±0.20°, 20.12±0.20°, and 24.13±0.20°.

In some embodiments of the present disclosure, the X-ray powder diffraction (XRPD) pattern of the crystalline form "A" is as shown in FIG. 1.

In some embodiments of the present disclosure, analytical data of the XRPD pattern of the crystalline form "A" are as shown in Table 1:

TABLE 1

| No. | 2θ angle (°) | D-spacing (Å) | Relative intensity (%) |
| --- | --- | --- | --- |
| 1 | 3.522 | 25.0663 | 21.4 |
| 2 | 6.038 | 14.6251 | 100 |
| 3 | 7.849 | 11.2539 | 4.3 |
| 4 | 12.110 | 7.3025 | 4.0 |
| 5 | 12.641 | 6.9968 | 1.7 |
| 6 | 14.398 | 6.1469 | 6.9 |
| 7 | 15.114 | 5.8570 | 9.0 |
| 8 | 15.691 | 5.6431 | 3.2 |
| 9 | 16.652 | 5.3193 | 4.0 |
| 10 | 18.206 | 4.8686 | 27.2 |
| 11 | 18.461 | 4.8021 | 10.1 |
| 12 | 18.799 | 4.7165 | 5.2 |
| 13 | 20.121 | 4.4096 | 8.2 |
| 14 | 22.980 | 3.8669 | 4.2 |
| 15 | 23.545 | 3.7754 | 3.1 |
| 16 | 24.127 | 3.6857 | 12 |
| 17 | 24.499 | 3.6305 | 4.8 |
| 18 | 25.411 | 3.5022 | 1.8 |
| 19 | 27.381 | 3.2546 | 2.1 |
| 20 | 27.967 | 3.1877 | 1.4 |
| 21 | 29.144 | 3.0615 | 1.5 |
| 22 | 33.335 | 2.6856 | 0.9 |

In some embodiments of the present disclosure, a differential scanning calorimetry curve of the crystalline form "A" has an endothermic peak starting at 155.36° C.±3° C.

In some embodiments of the present disclosure, the differential scanning calorimetry (DSC) curve of the crystalline form "A" is as shown in FIG. 2.

In some embodiments of the present disclosure, a thermal gravimetric analysis curve of the crystalline form "A" has a weight loss of 0.1489% at 100.00° C.±3° C.

In some embodiments of the present disclosure, the thermal gravimetric analysis (TGA) curve of the crystalline form "A" is as shown in FIG. 3.

The present disclosure also provides a method for preparing the crystalline form "A" of the compound represented by formula (I), comprising steps of:

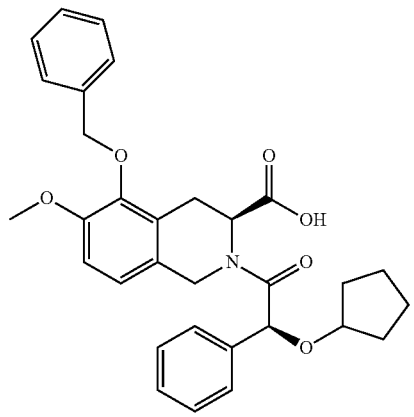

(I)

(a) dissolving the compound represented by formula (I) in a mixed solvent to obtain a first mixture;

(b) stirring the first mixture at 30~50° C. for 10-30 hours to obtain a second mixture; and (c) filtering the second mixture to obtain a filter cake, and then drying the filter cake at 30-50° C. for 15-25 hours;

wherein, the mixed solvent is a mixture of acetone and water at a volume ratio of 1:(1.5-2.5).

The present disclosure also provides a crystalline form "B" of a compound represented by formula (I), wherein an X-ray powder diffraction pattern of the crystalline form "B" has characteristic diffraction peaks at the following 2θ angles: 6.08±0.20°, 12.12±0.20°, and 18.19±0.20°.

In some embodiments of the present disclosure, the X-ray powder diffraction pattern of the crystalline form "B" has characteristic diffraction peaks at the following 2θ angles: 6.08±0.20°, 12.12±0.20°, 18.19±0.20°, 24.31±0.20°, and 30.50±0.20°.

In some embodiments of the present disclosure, the X-ray powder diffraction pattern of the crystalline form "B" has characteristic diffraction peaks at the following 2θ angles: 3.52±0.20°, 6.08±0.20°, 9.25±0.20°, 12.12±0.20°, 14.00±0.20°, 18.19±0.20°, 24.31±0.20°, and 30.50±0.20°.

In some embodiments of the present disclosure, the X-ray powder diffraction pattern of the crystalline form "B" is as shown in FIG. 4.

In some embodiments of the present disclosure, analytical data of the XRPD pattern of the crystalline form "B" are as shown in Table 2:

TABLE 2

| No. | 2θ angle (°) | D-spacing (Å) | Relative intensity (%) |
|---|---|---|---|
| 1 | 3.521 | 25.0708 | 4.1 |
| 2 | 6.078 | 14.5287 | 54.2 |
| 3 | 9.25 | 9.553 | 5.7 |
| 4 | 12.116 | 7.2991 | 100 |
| 5 | 12.703 | 6.9629 | 1.6 |
| 6 | 14.003 | 6.3194 | 4.3 |
| 7 | 18.192 | 4.8726 | 70.7 |
| 8 | 19.417 | 4.5678 | 1.8 |
| 9 | 20.929 | 4.2411 | 2.1 |
| 10 | 24.31 | 3.6583 | 9.2 |
| 11 | 25.335 | 3.5126 | 2.4 |

TABLE 2-continued

| No. | 2θ angle (°) | D-spacing (Å) | Relative intensity (%) |
|---|---|---|---|
| 12 | 30.503 | 2.9282 | 10.8 |
| 13 | 31.381 | 2.8483 | 3.7 |

In some embodiments of the present disclosure, a differential scanning calorimetry curve of the crystalline form "B" has an endothermic peak starting at 150.95° C.±3° C.

In some embodiments of the present disclosure, the differential scanning calorimetry curve of the crystalline form "B" is as shown in FIG. 5.

In some embodiments of the present disclosure, a thermal gravimetric analysis curve of the crystalline form "B" has a weight loss of 0.0558% at 120.00° C.±3° C.

In some embodiments of the present disclosure, the thermal gravimetric analysis curve of the crystalline form "B" is as shown in FIG. 6.

The present disclosure also provides a method for preparing the crystalline form "B" of the compound represented by formula (I), comprising steps of:

(a) adding the compound represented by formula (I) to a solvent to obtain a first suspension;

(b) stirring the suspension at 35-45° C. for 30-60 hours to obtain a second suspension; and (c) centrifuging the second suspension to obtain a filter cake, and then drying the filter cake for 8-16 hours;

wherein, the solvent is selected from the group consisting of methanol, ethanol and acetonitrile; or the solvent is a mixture of acetone and water at a volume ratio of 3:2.

The present disclosure also provides use of the crystalline form "A" or the crystalline form "B" in the preparation of drugs for treating chronic pain.

The present disclosure also provides a method for preparing a compound represented by formula (I),

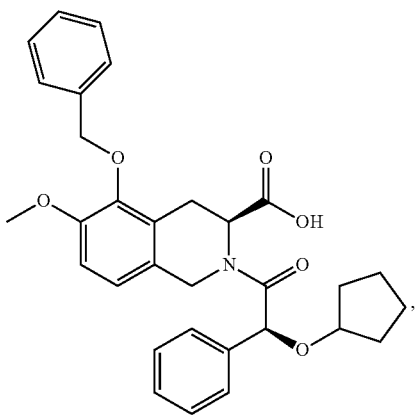

(I)

comprising steps of:

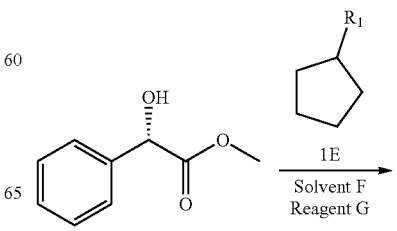

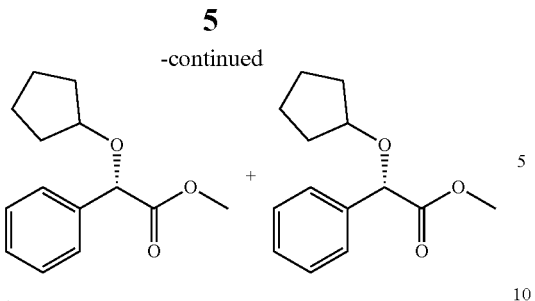

wherein,

R1 is selected from Cl, Br and I;

solvent F is selected from n-heptane, dichloromethane, tetrahydrofuran, cyclohexane and dioxane; and reagent G is selected from silver oxide, magnesium sulfate, calcium sulfate and sodium sulfate.

In some embodiments of the present disclosure, the method comprises steps of:

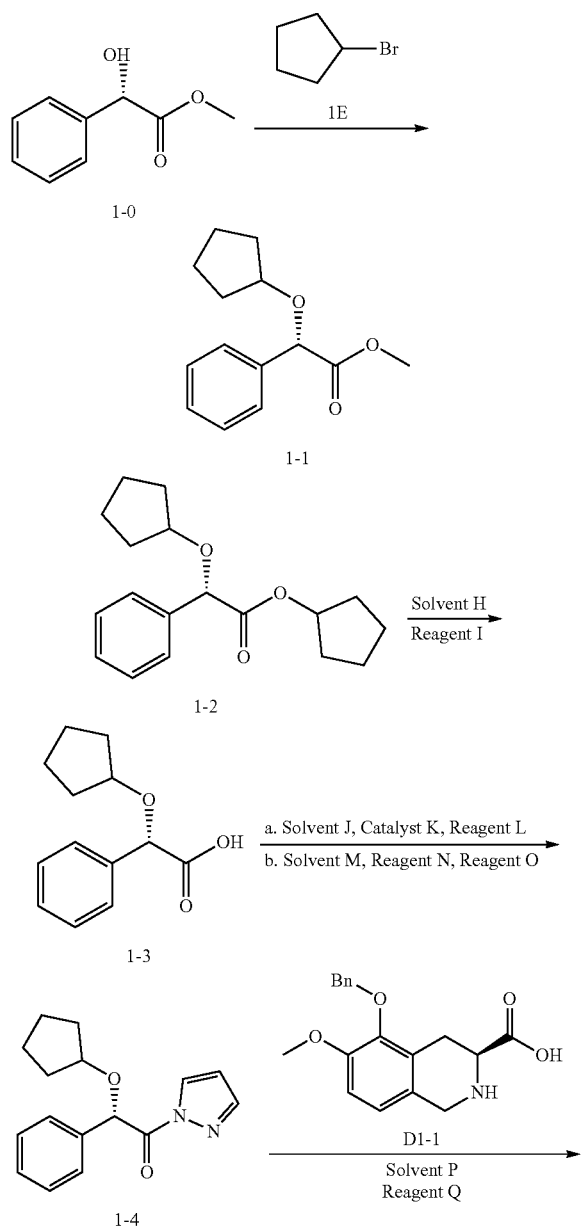

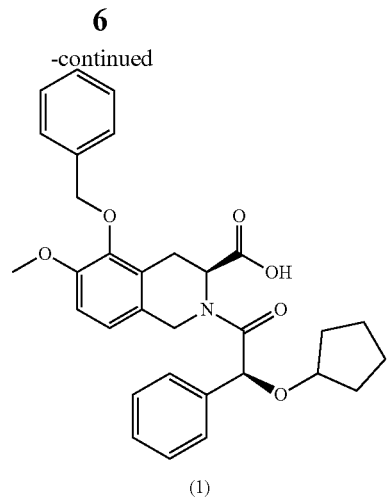

wherein, solvent H is selected from tetrahydrofuran, methanol and water;

reagent I is selected from lithium hydroxide monohydrate and sodium hydroxide;

solvent J is selected from dichloromethane;

catalyst K is selected from N,N-dimethylformamide;

reagent L is selected from oxalyl chloride;

solvent M is selected from dichloromethane;

reagent N is selected from pyrazole;

reagent O is selected from N-methylmorpholine;

solvent P is selected from N,N-dimethylformamide, dimethyl sulfoxide, dichloromethane and tetrahydrofuran; and reagent Q is selected from tetramethylguanidine, 1,8-diazabicycloundec-7-ene, triethylamine, diisopropylethylamine and 2,6-lutidine.

In some embodiments of the present disclosure, a molar ratio of compound 1E to compound 1-0 is (1.2-5):1.

In some embodiments of the present disclosure, a molar ratio of compound 1-4 to compound D1-1 is (1.1-1.5):1.

In some embodiments of the present disclosure, reaction systems for preparing compounds 1-1, 1-2 and 1-3 are controlled at a temperature of 25±5° C.

In some embodiments of the present disclosure, preparing the compound 1-4 comprises steps a and b, wherein a reaction system in the step a is controlled to a temperature of 25±5° C.; and a reaction system in the step b is controlled to a temperature of 5±5° C. when feeding reagents into the reaction system, and the reaction system is controlled to a temperature of 25±5° C. after the reagents feeding is completed.

In some embodiments of the present disclosure, the solvent F is selected from n-heptane, a ratio of n-heptane by volume to compound 1-0 by weight being (8.0-10.0):1, and the reagent G is selected from silver oxide and magnesium sulfate, a molar ratio of silver oxide and magnesium sulfate to compound 1-0 being (1.0-5.0):1.

In some embodiments of the present disclosure, the reagent G is fed in batches.

In some embodiments of the present disclosure, the solvent H is a mixture of tetrahydrofuran and water at a volume ratio of (1-2):1, the reagent I is lithium hydroxide monohydrate, wherein a molar ratio of lithium hydroxide monohydrate to compound 1-0 is (1.0-2.0):1, a weight ratio of solvent J to compound 1-3 is 10:1, a molar ratio of catalyst K to compound 1-3 is (0.002-0.004):1, a molar ratio of reagent L to compound 1-3 is (1.2-2.0):1, a weight ratio of solvent M to compound 1-3 is (6-10):1, a molar ratio of reagent N to compound 1-3 is (1.0-1.5):1, and a molar ratio of reagent O to compound 1-3 is (1.0-1.5):1; and solvent P is selected from N,N-dimethylformamide, wherein a weiht ratio of N,N-dimethylformamide to compound 1-4 is 10:1; and the reagent Q is selected from tetramethylguanidine, wherein a molar ratio of tetramethylguanidine to compound 1-4 is (1-1.2):1.

Technical Effects

The compounds of the present disclosure exhibit good biological activity in vitro, and exhibit excellent pharmacokinetic properties in various genera. Crystalline form of the compounds is stable and has weak hygroscopicity.

DEFINITION AND DESCRIPTION

Unless otherwise stated, the following terms and phrases as used herein are intended to have the following meanings. A particular term or phrase should not be considered undefined or unclear without a particular definition, but should be understood in the ordinary sense. When a trade name appears herein, it is intended to refer to its corresponding commodity or its active ingredient.

The intermediate compounds of the present disclosure can be prepared by a variety of synthetic methods well known to those skilled in the art, including the embodiments listed below, the embodiments formed by combining with other chemical synthesis methods, and equivalent alternatives well known to those skilled in the art. Preferred embodiments include but are not limited to the embodiments of the present disclosure.

The chemical reactions in the embodiments of the present disclosure are completed in a suitable solvent which is suitable for the chemical change of the present disclosure and the required reagents and materials. In order to obtain the compounds of the present disclosure, it is sometimes necessary for those skilled in the art to modify or select the synthesis steps or reaction schemes based on the existing embodiments.

Hereinafter, the present disclosure is described in detail below by referring to the examples, which are not intended to adversely limit the present disclosure.

All solvents used in the present disclosure are commercially available and can be used without further purification.

The present disclosure employs the following abbreviations: r.t. represents room temperature; THF represents tetrahydrofuran; NMP represents N-methylpyrrolidone; $MeSO_3H$ represents methanesulfonic acid; DME represents ethylene glycol dimethyl ether; DCM represents dichloromethane; Xphos represents 2-bicyclohexylphosphine-2'4'6'-triisopropylbiphenyl; EtOAc represents ethyl acetate; MeOH represents methanol; acetone represents acetone; 2-Me-THF represents 2-methyltetrahydrofuran; IPA represents isopropanol; and HATU represents 2-(7-azobenzotriazole)-N,N,N',N'-tetramethylurea hexafluorophosphate.

Compounds are named manually or by ChemDraw® software, and commercially available compounds are named supplier catalog names.

X-Ray Powder Diffractometer (XRPD) Method of the Present Disclosure

Instrument model: Bruker D8 advance X-ray diffractometer

Test method: about 10-20 mg sample is used for XRPD detection.

The detailed parameters of XRPD are as follows:
X-Ray tube: Cu, kα, (λ=1.54056Å).
Voltage of the X-Ray tube: 40 kV, current of the X-Ray tube: 40 mA
Divergence slit: 0.60 mm
Detector slit: 10.50 mm
Antiscattering slit: 7.10 mm
Scanning range: 3-40 deg or 4-40 deg
Step diameter: 0.02 deg
Step size: 0.12 seconds
Speed of Sample tray: 15 rpm Differential Scanning Calorimeter (DSC) Method of the Present Disclosure Instrument model: TA Q2000 Differential Scanning calorimeter Test method: DSC test is carried out by placing a sample (about 1 mg) in an aluminum crucible, and heating the sample to raise the temperature from room temperature to 250° C. (or 280° C.) at a rate of 10° C./min under 50 mL/min N2 conditions.

Thermal Gravimetric Analyzer (TGA) Method of the Present Disclosure

Instrument model: TA Q5000 thermal gravimetric analyzer

Test method: The TGA test is carried out by placing a sample (2-5 mg) in a platinum crucible, and heating the sample to raise the temperature from room temperature to 30° C. (or 280° C.) or to a temperature when the weight loss is 20%, at a rate of 10° C./min under 25 mL/min N2 conditions.

Dynamic Vapor Sorption (DVS) Method of the Present Disclosure

Instrument model: SMS DVS Advantage dynamic vapor adsorber

Test conditions: a sample (10-15 mg) is placed in DVS sample tray for testing.

The detailed DVS parameters are as follows:
Temperature: 25° C.
Balance: dm/dt=0.01%/min (shortest: 10 min, longest: 180 min)
Drying: drying for 120 min at 0% RH
RH (%) test gradient: 10%
RH (%) test gradient range: 0%-90%-0%

The hygroscopicity property is evaluated and classified as follows:

| Classification of hygroscopicity | Weight gain caused by hygroscopicity * |
|---|---|
| Deliquescence | Absorbing enough water to form a liquid |
| Very hygroscopic | ΔW % ≥ 15% |
| hygroscopic | 15% > ΔW % ≥ 2% |
| Slightly hygroscopic | 2% > ΔW % ≥ 0.2% |
| No or substantially no hygroscopicity | ΔW % < 0.2% |

* Weight gain caused by hygroscopicity at 25° C. and 80% RH

High Performance Liquid Chromatograph (HPLC) Method of the Present Disclosure

The detailed parameters are as follows:

| Column model | Agilent Eclipse Plus C18 4.6 × 150 mm, 3.5 μm |
|---|---|
| Flow rate | 1.0 ml/min |
| Detection wavelength | 210 nm |
| Column temperature | 40° C. |
| Injection volume | 2 mL, 10 mL |
| Running time | 62 min |

-continued

| Mobile phase | Mobile phase A: 0.04% phosphoric acid aqueous solution Mobile Phase B: Acetonitrile |  |
|---|---|---|
| Diluent | Acetonitrile: Water (50:50) |  |
| Gradient | Time (min) | Mobile phase A (%) | Mobile phase B (%) |
| | 0.01 | 90 | 10 |
| | 50 | 10 | 90 |
| | 55 | 10 | 90 |
| | 57 | 90 | 10 |
| | 62 | 90 | 10 |

DETAILED DESCRIPTION

Figure 1:
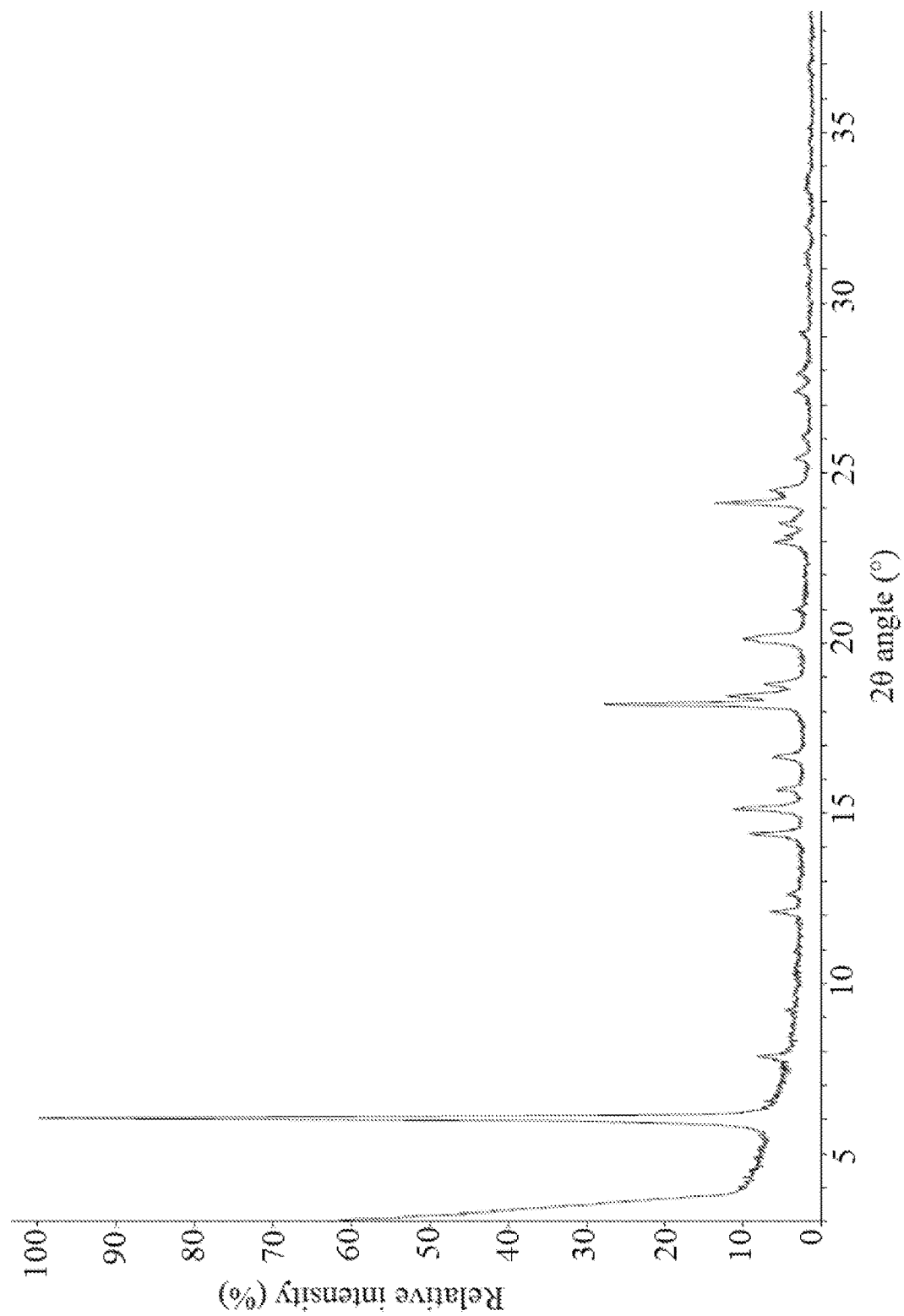
FIG. 1 is an XRPD pattern of Cu-Kα radiation of the crystalline form "A" of a compound represented by formula (I)
Figure 2:
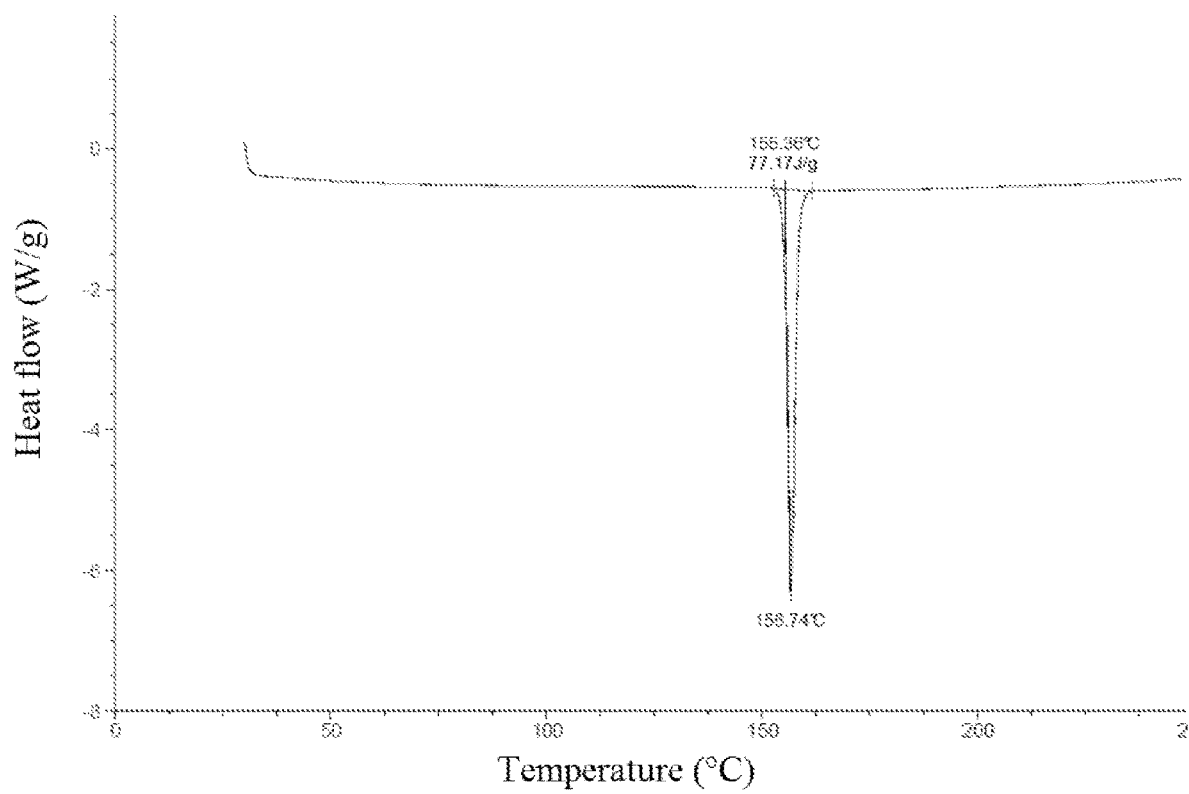
FIG. 2 is a DSC pattern of the crystalline form "A" of a compound represented by formula (I)
Figure 3:
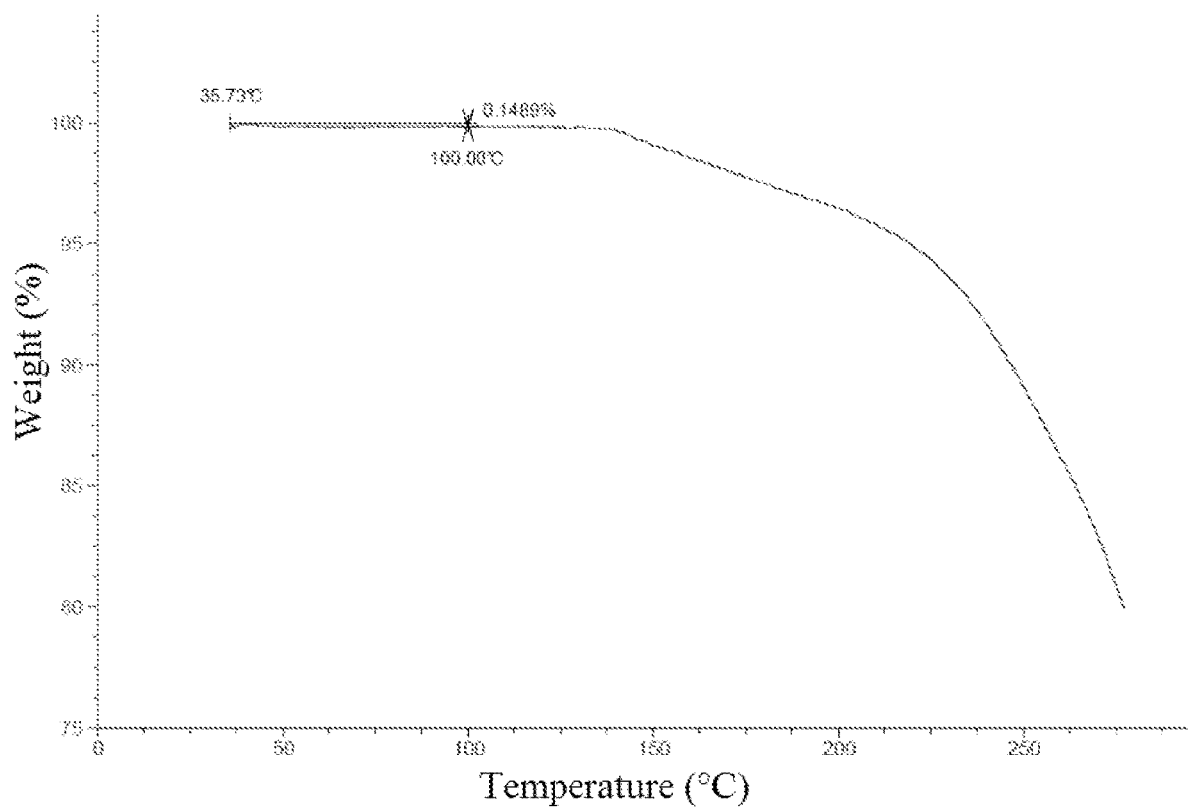
FIG. 3 is a TGA pattern of the crystalline form "A" of a compound represented by formula (I)
Figure 4:
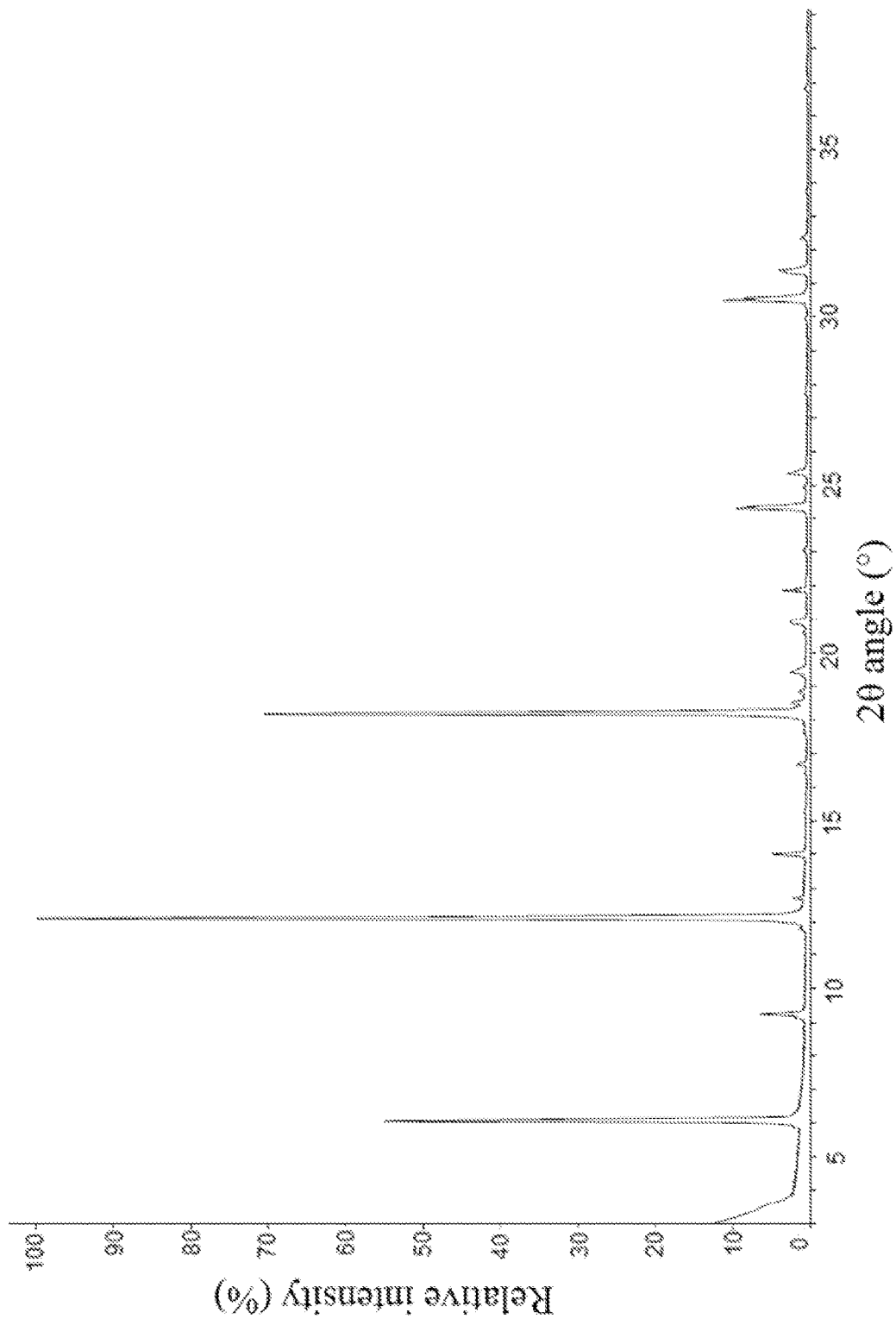
FIG. 4 is an XRPD pattern of Cu-Kα radiation of the crystalline form "B" of a compound represented by formula (I)
Figure 5:
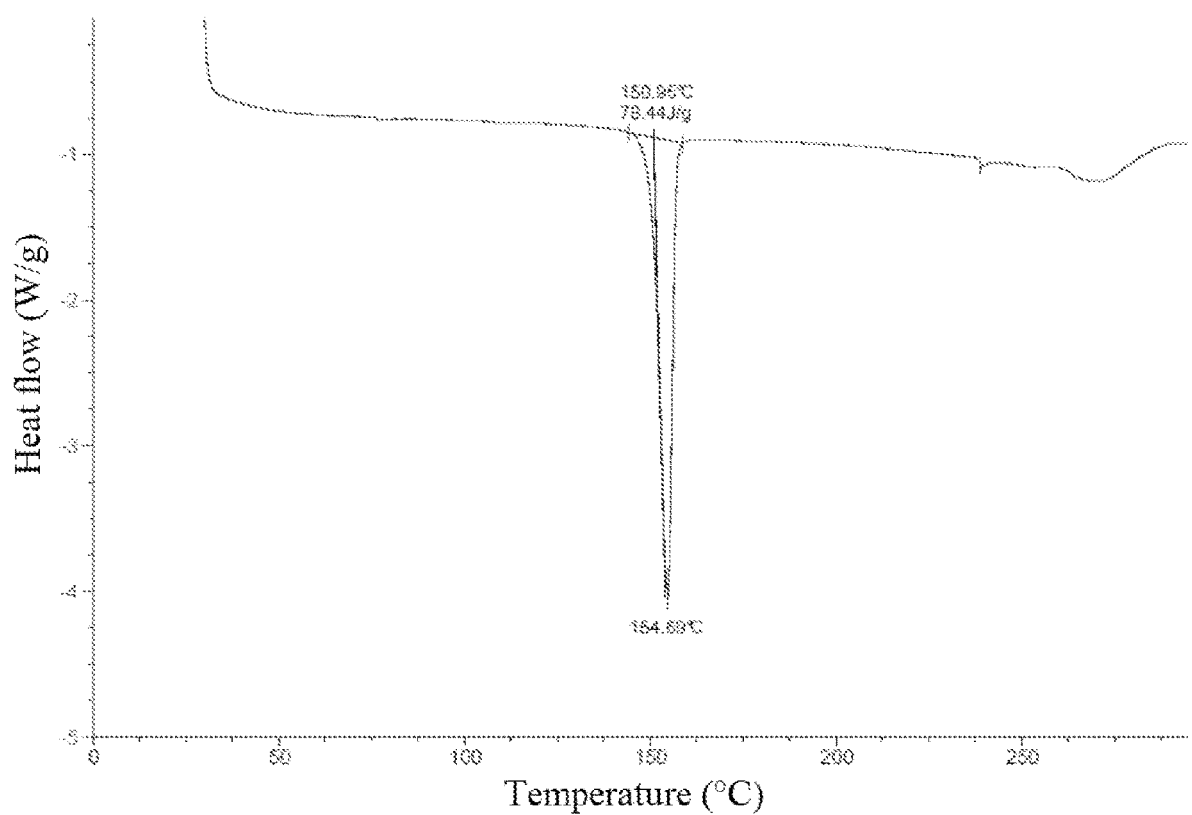
FIG. 5 is a DSC pattern of the crystalline form "B" of a compound represented by formula (I)
Figure 6:
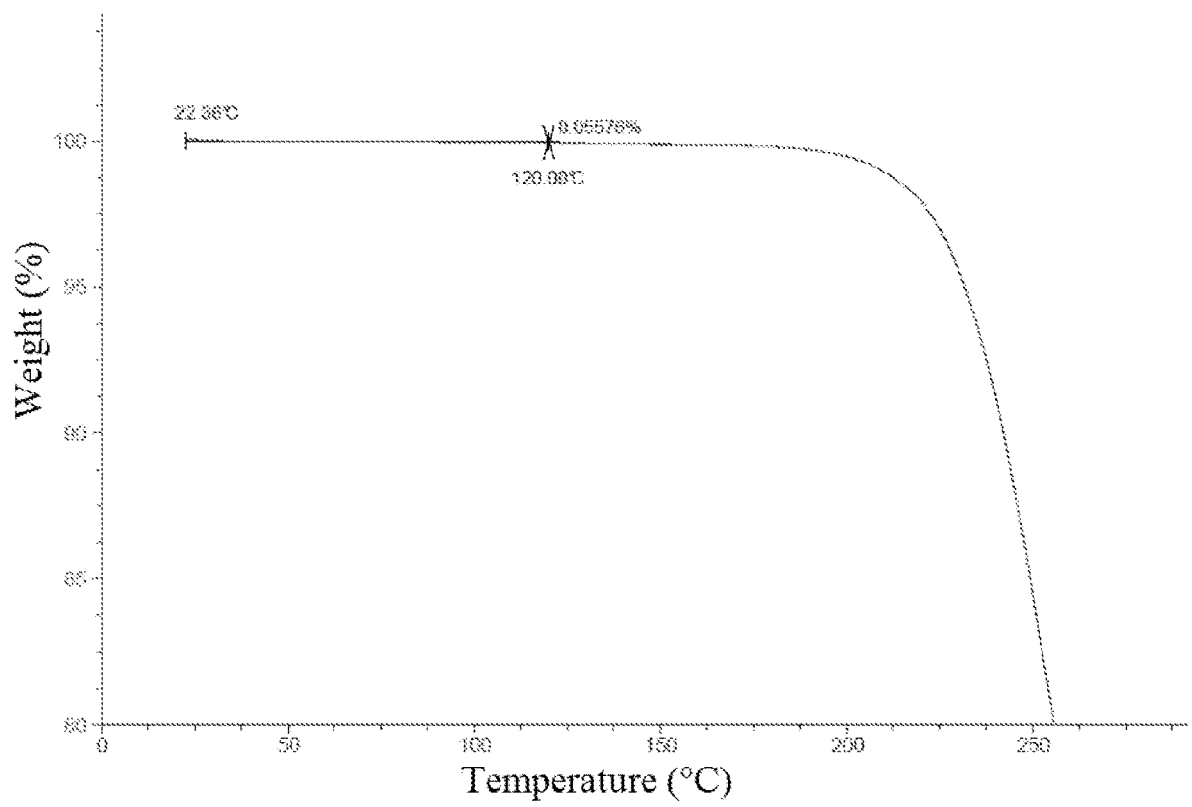
FIG. 6 is a TGA pattern of the crystalline form "B" of a compound represented by formula (I)
Figure 7:
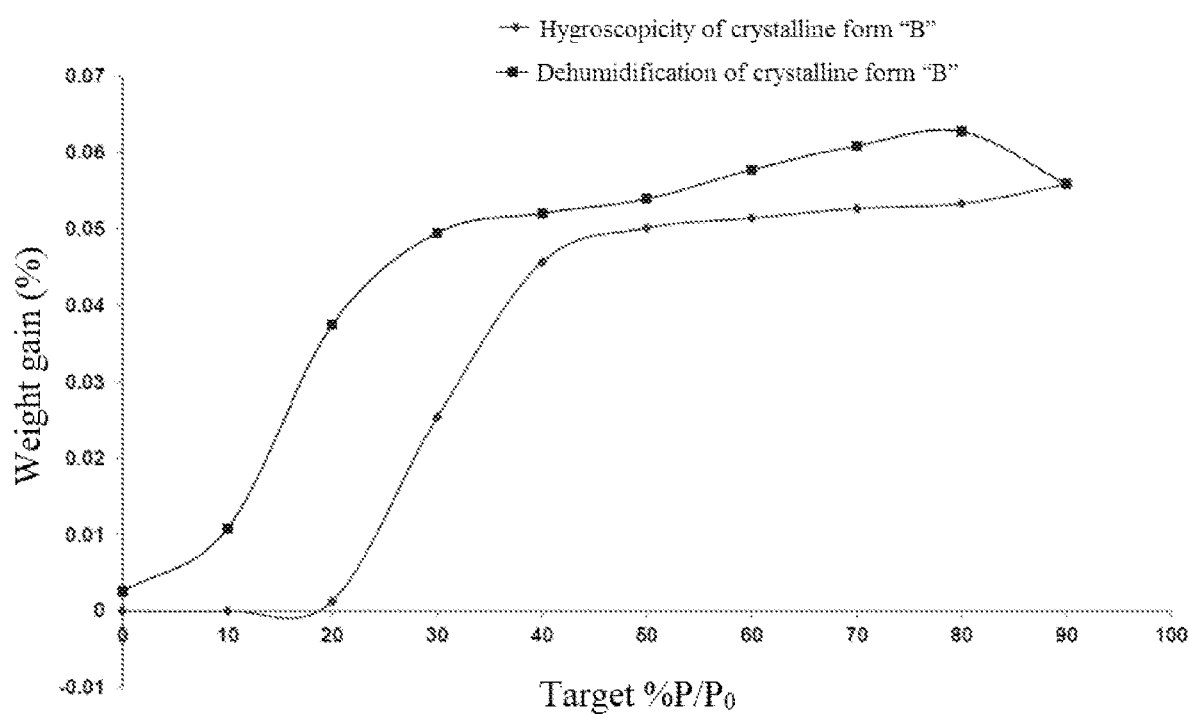
FIG. 7 is a DVS pattern of the crystalline form "B" of a compound represented by formula (I).

In order to better understand the content of the present disclosure, the present disclosure is further described in detail below by referring to the examples, which are not intended to adversely limit the present disclosure.

Reference Example 1: Preparation of Compound S-A1

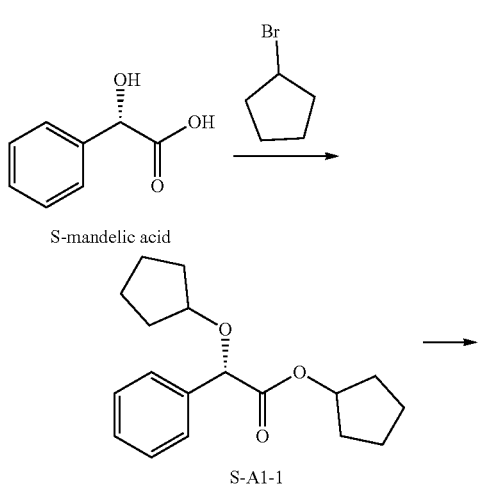

-continued

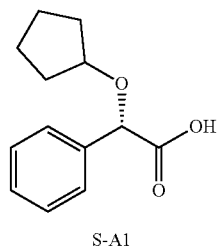

S-A1

Step 1: Preparation of Compound S-A1-1

Silver oxide (1.5 g, 6.6 mmol) was added to a mixture of S-mandelic acid (500.0 mg, 3.3 mmol) and bromocyclopentane (49.0 g, 328.6 mmol), and stirred at 20-25° C. for 16 hours to obtain a reaction solution. The reaction solution was filtered to obtain a filtrate, and the filtrate was concentrated under vacuum for removing the solvent, so as to obtain a crude product. The crude product was separated and purified by silica gel chromatography column (eluent: ethyl acetate/petroleum ether 0-10%) to obtain compound S-A1-1. $^1$H NMR (400 MHz, CDCl$_3$): δ 7.49-7.40 (m, 2H), 7.38-7.28 (m, 3H), 5.22-5.19 (m, 1H), 4.88 (s, 1H), 4.03-3.99 (m, 1H), 1.89-1.64 (m, 10H), 1.57-1.45 (m, 6H). MS m/z: 311.1 [M+Na]$^+$.

Step 2: Preparation of Compound S-A1

Compound S-A1-1 (340.0 mg, 1.2 mmol) was dissolved in a mixed solvent of tetrahydrofuran (6.0 mL) and water (3.0 mL), and then lithium hydroxide monohydrate (283.0 mg, 11.8 mmol) was added thereto and stirred at 20-25° C. for 48 hours to obtain a reaction solution. The reaction solution was adjusted to pH<3 with 1 N hydrochloric acid, and then was extracted with ethyl acetate (20 mL×3) to obtain organic phases. The organic phases were combined and washed with saturated saline solution (50 mL), dried with anhydrous sodium sulfate, and concentrated under vacuum to obtain a crude product. The crude product was separated and purified by silica gel chromatography column (eluent: 0-37.5% petroleum ether/ethyl acetate) to obtain compound S-A1. $^1$H NMR (400 MHz, CDCl$_3$): δ 7.45-7.34 (m, 5H), 4.93 (s, 1H), 4.07-4.03 (m, 1H), 1.78-1.69 (m, 6H), 1.62-1.48 (m, 2H). SFC: Column: ChiralCel OJ-H (150 mm*4.6 mm, 5um); Mobile phase: A: CO$_2$, B: Ethanol [0.05% diethylamine]; B %: 5%-40% 5.5 min, 40% 3 min, 5%1.5 min; Rt=2.321 min; 95.6% ee.

Reference Example 2: Preparation of Compound (−)-C1

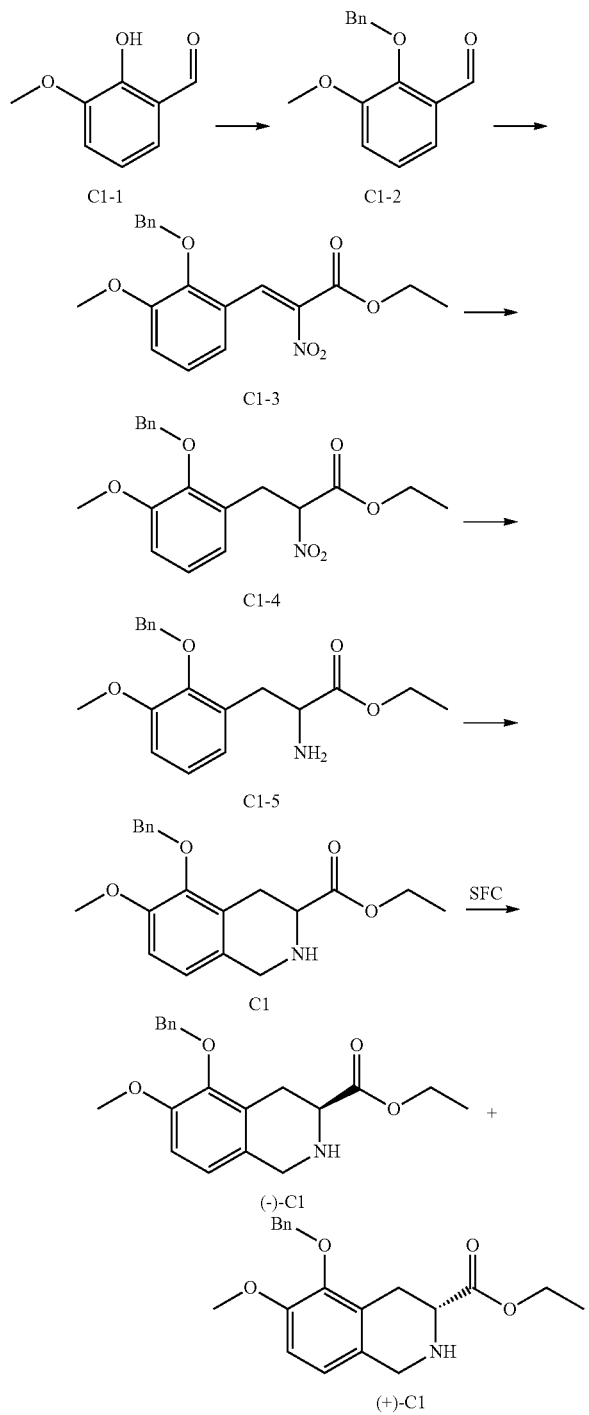

Step 1: Preparation of Compound C1-2

Under the protection of nitrogen, compound C1-1 (200.0 g, 1.31 mol) was dissolved in absolute ethanol (1.50 L). Anhydrous potassium carbonate (181.1 g, 1.31 mol) and benzyl bromide (268.9 g, 1.57 mol) were successively added thereto under stirring at 15° C. to obtain a reaction solution. The reaction solution was heated to 100° C. and stirred for 15 hours at this temperature. Then the reaction solution was cooled to room temperature, and was filtered to obtain a filtrate. The filtrate was concentrated under vacuum to obtain an oily substance. The oily substance was re-dissolved with ethyl acetate (3.0 L), washed successively with 2N sodium hydroxide aqueous solution (500 mL×2) and saturated saline solution (600 mL×2), dried with anhydrous sodium sulfate, filtered, and concentrated under vacuum to obtain a crude product. The crude product was dispersed in petroleum ether, stirred for 1 hour, and filtered to obtain compound C1-2. $^1$H NMR (400 MHz, CDCl$_3$): δ 10.25 (s, 1H), 7.42-7.34 (m, 6H), 7.21-7.12 (m, 2H), 5.19 (s, 2H), 3.96 (s, 3H).

Step 2: Preparation of Compound C1-3

Under the protection of nitrogen, a mixed solution of compound C1-2 (220.0 g, 908.08 mmol), ethyl 2-nitroacetate (145.0 g, 1.09 mol) and diethylamine hydrochloride (149.3 g, 1.36 mol) in anhydrous toluene (2.1 L) was heated to 130° C. and refluxed for 15 hours at this temperature to obtain a reaction solution. The reaction solution was treated with Deane-Stark to remove water. Then the reaction solution was cooled to room temperature, and then was concentrated under vacuum to remove toluene, obtaining a residue. The residue was re-dissolved in dichloromethane (500 mL), washed with saturated saline solution (1000 mL×2), dried with anhydrous sodium sulfate, filtered, and concentrated under vacuum to obtain a crude compound C1-3, which was used directly in the next reaction without purification.

Step 3: Preparation of Compound C1-4

Under the protection of nitrogen, the crude compound C1-3 (430.0 g, 1.2 mol) obtained in step 2 above was dissolved in isopropanol (2.2 g, 36.0 mmol) and chloroform (4.5 L) to obtain a mixed solution. The mixed solution was cooled to 0° C., silica gel (1.8 kg) of 100-200 mesh was added thereto under stirring, and then sodium borohydride (201.1 g, 5.3 mol) was added thereto in batches within 1.5 hours to obtain a reaction solution. The reaction solution was heated to 15° C., and then stirred constantly for 12 hours. Acetic acid (210 mL) was added thereto slowly and stirring was performed for 15 minutes. The reaction solution was filtered to obtain a filter cake and a filtrate. The filter cake was washed with dichloromethane (500 mL) to obtain a filtrate. The filtrates were combined and concentrated under vacuum to obtain a residue. The residue was separated and purified by silica gel chromatography column (eluent: 6%-10% petroleum ether/ethyl acetate) to obtain compound C1-4. $^1$H NMR (400 MHz, CDCl$_3$): δ 7.48-7.33 (m, 5H), 7.02-6.97 (m, 1H), 6.94-6.90 (m, 1H), 6.64-6.62 (dd, J=1.6, 7.6 Hz, 1H), 5.33-5.30 (dd, J=6.0, 9.2 Hz, 1H), 5.19-5.05 (m, 2H), 4.15-4.10 (q, J=7.2 Hz, 2H), 3.91 (s, 3H), 3.44-3.31 (m, 2H), 1.16-1.12 (t, J=7.2 Hz, 3H).

Step 4: Preparation of Compound C1-5

Compound C1-4 (76.2 g, 212.04 mmol) was dissolved in acetic acid (700 mL) at 15° C., and then zinc powder (110.9 g, 1.70 mol) was slowly added thereto to obtain a reaction solution. The reaction solution was maintained at a temperature between 60-65° C., and then was stirred at 60° C. for 2 hours. Then the reaction solution was cooled to room temperature, and was filtered to obtain a filter cake and a filtrate. The filter cake was washed with acetic acid (300 mL)

to obtain a filtrate. The filtrates were combined and concentrated under vacuum to obtain a residue. The residue was re-dissolved in dichloromethane (500 mL), washed with saturated aqueous sodium bicarbonate solution (200 mL×2) and saturated saline solution (200 mL×2), dried with anhydrous sodium sulfate, filtered, and concentrated under vacuum to obtain a crude product C1-5, which was used directly in the next step without purification. MS m/z: 330.1 [M+1]⁺.

Step 5: Preparation of Compound C1

Under the protection of nitrogen at 15° C., compound C1-5 (48.9 g, 149.4 mmol) was dissolved in 2N hydrochloric acid solution (500 mL), then 37% aqueous formaldehyde solution (36.4 g, 448.1 mmol) was added thereto to obtain a reaction solution. The reaction solution was stirred for 25 hours, and filtered to obtain a filter cake. The filter cake was washed with water (100 mL) and dried under vacuum to obtain hydrochloride salt of compound C1. MS m/z: 342.1 [M+1]⁺.

Step 6: Preparation of Compound (−)-C1 and (+)-C1

Compound C1 (40.0 g, 117.2 mmol) was separated by chiral column to obtain two isomers (−)-C1 and (+)-C1.

(−)-C1: ¹H NMR (400 MHz, CDCl₃): δ 7.40-7.38 (m, 2H), 7.33-7.22 (m, 3H), 6.73-6.71 (m, 2H), 4.93-4.92 (m, 2H), 4.17-4.15 (q, J=7.2 Hz, 2H), 4.10-3.93 (m, 2H), 3.79 (s, 3H), 3.62-3.58 (m, 1H), 3.07-3.06 (m, 1H), 2.77-2.65 (m, 1H), 1.21 (t, J=7.2 Hz, 3H). MS m/z: 342.1 [M+1]⁺. [α]=−23.4.

(+)-C1: ¹H NMR (400 MHz, CDCl₃): δ 7.43-7.40 (m, 2H), 7.33-7.22 (m, 3H), 6.86 (s, 2H), 5.06-4.95 (q, J=11.2 Hz, 2H), 4.54-4.50 (m, 1H), 4.33-4.21 (m, 3H), 4.07-4.05 (m, 1H), 3.88 (s, 3H), 3.34-3.25 (m, 1H), 3.20-3.14 (m, 1H), 1.30-1.26 (t, J=7.2 Hz, 3H). MS m/z: 342.1 [M+1]⁺. [α]=+9.8.

Reference Example 3: Preparation of Compound D1

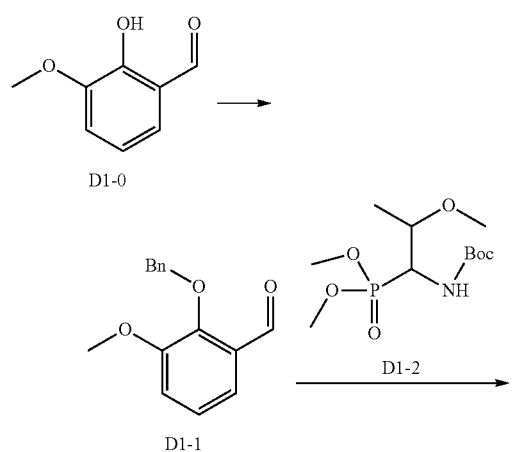

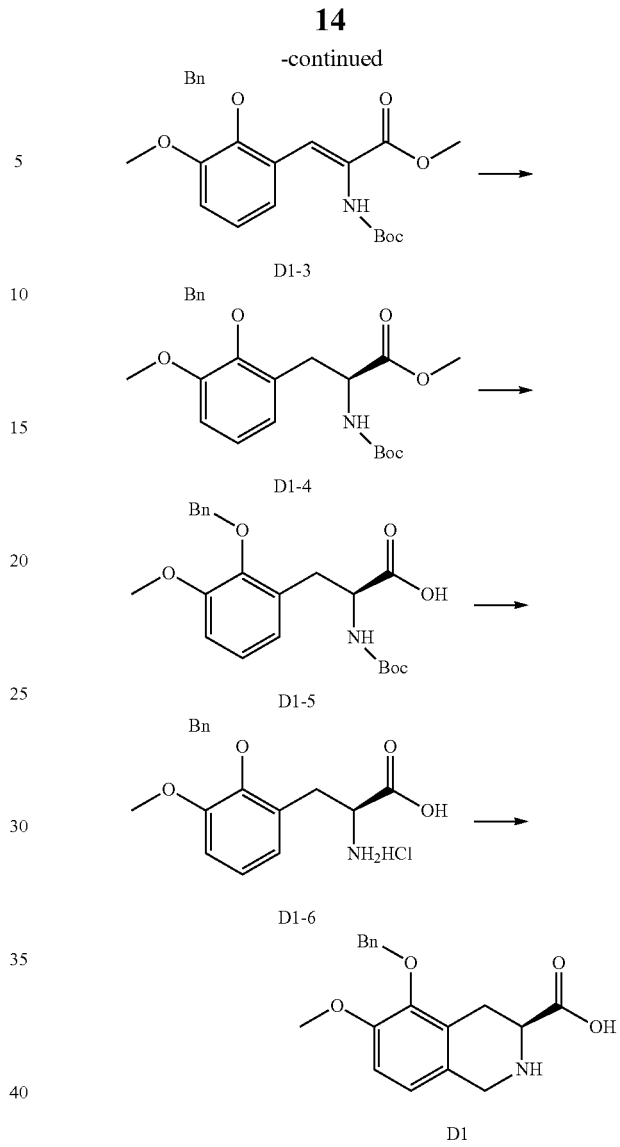

Step 1: Preparation of Compound D1-1

Acetone (21.2 L) was added to a 50 L reactor, then stirring was started, and starting materials D1-0 (2.69 kg), potassium carbonate (3.48 kg) and benzyl bromide (3.39 kg) were successively added to the reactor to obtain a reaction solution. The reaction solution was stirred at 55-60° C. for about 18 hours, then was cooled to 10-20° C., and filtered under reduced pressure to obtain a filter cake and a filtrate. The filter cake was washed with acetone (2 L, 1.5 L) to obtain a filtrate. The filtrates were transferred to a rotary evaporator and concentrated under reduced pressure at an external temperature of 40-45° C. to obtain a crude product. The crude product was dissolved in ethyl acetate (26 L) and washed successively with 13 L water twice (6.5 L each time) and 13 L saturated sodium chloride aqueous solution twice (6.5 L each time). The organic phases were dried with anhydrous sodium sulfate (1.5 kg), filtered to obtain a filtrate which was concentrated under reduced pressure at an external temperature of 40-45° C. and combined with the filtrate obtained in another batch to obtain a crude product. The crude product was added to 30 L of petroleum ether, stirred for 21 hours at an external temperature of 0-5° C., and filtered to obtain a filter cake which was washed twice with 4 L of petroleum ether (2 L each time) to produce a further filter cake which was separated and purified by silica gel column chromatography (eluent: 0-10% ethyl acetate/petroleum ether) to obtain compound D1-1.

$^1$H NMR (400 MHz, CDCl$_3$): δ 10.25 (s, 1H), 7.41-7.36 (m, 6H), 7.17-7.07 (m, 2H), 5.19 (s, 2H), 3.95 (s, 3H)

Step 2: Preparation of Compound D1-3

Tetrahydrofuran (5.0 L) was added to a 50 L reactor, then stirring was started, and starting materials D1-2 (3.21 kg) and tetramethylguanidine (1.31 kg) were successively added to the reactor. The temperature was cooled down. Solution of a raw material A-1 (2.3 kg) in tetrahydrofuran (4.8 L) was added dropwise thereto to obtain a reaction solution. The reaction solution was maintained at internal temperature (i.e. a temperature of the reaction solution) not exceeding 10° C., stirred at 20-30° C. for about 16 hours, and concentrated under reduced pressure with a rotary evaporator at an external temperature (i.e. a temperature of water bath in the rotary evaporator) of 35-40° C. to obtain a crude product. The crude product was dissolved in ethyl acetate (20 L), washed successively with 8 L of 10% citric acid aqueous solution and 10 L of saturated sodium chloride aqueous solution twice (5 L each time) to obtain organic phases. The organic phases were dried with anhydrous sodium sulfate (1.0 kg), and filtered to obtain a filtrate. The filtrate was concentrated under reduced pressure at an external temperature of 35-40° C. to obtain a crude product which was separated and purified by silica gel column chromatography (eluent: 0-30% ethyl acetate/Petroleum ether) to obtain compound D1-3.

$^1$H NMR (400 MHz, CDCl$_3$): δ 7.38-7.32 (m, 5H), 7.08-7.03 (m, 2H), 6.94-6.91 (m, 1H), 4.98 (s, 2H), 3.90 (s, 3H), 3.84 (s, 3H), 1.39 (s, 9H).

Step 3: Preparation of Compound D1-4

Bis(1,5-cyclooctadiene)-trifluoromethanesulfonate rhodium(I) (249.20 mg) and (+)-1,2-bis[(2S,5S)-2,5-diethyl-1-phosphorous]benzene (210.40 mg) were dissolved in methanol (20 mL), and the resulted mixture was stirred under nitrogen protection for 15 minutes, and then added to a solution of compound D1-3 (200 g) in methanol (1 L) under argon atmosphere to obtain a reaction solution. The reactor was replaced with argon three times and then replaced with hydrogen three times, and the reaction solution was stirred for 18 hours under hydrogen (50 psi) atmosphere at 20-25° C. The pressure was reduced to remove organic solvents, obtaining a crude product which was combined with crude products obtained in other batches and filtered through silica gel to obtain compound D1-4.

$^1$H NMR (400 MHz, CDCl$_3$): δ 7.54-7.46 (m, 2H), 7.41-7.35 (m, 3H), 7.03-7.00 (m, 1H), 6.90-6.86 (m, 1H), 6.76-6.74 (m, 1H), 5.35-5.32 (m, 1H), 5.05 (s, 2H), 4.49-4.44 (m, 1H), 3.90 (s, 3H), 3.62 (s, 3H), 3.06-2.95 (m, 2H), 1.39 (s, 9H). SFC: Column: Lux Cellulose-2 (150 mm*4.6 mm, 3 um); Mobile phase: B: Isopropanol [0.05% ethylamine]; B %: 5%-40% 5.5 min, 40% 3 min, 5% 1.5 min; Rt=3.247 min; 97.8% ee.

Step 4: Preparation of Compound D1-5

Lithium hydroxide monohydrate (0.76 kg) was dissolved in water (16.0 L), and a solution of compound A-4 (3.69 kg) in tetrahydrofuran (10.6 L) was added dropwise thereto to obtain a reaction solution. The reaction solution was maintained at internal temperature not exceeding 15° C., stirred at 10-20° C. for 18 hours. pH was adjusted to about 5 with saturated citric acid aqueous solution. The pressure was reduced to remove organic solvents, obtaining a crude product. The crude product was added to 16.0 L ethyl acetate, and separation is performed to obtain an organic phase. The organic phase was successively washed with 10% citric acid aqueous solution (8 L) and 10% sodium chloride aqueous solution three times (6.0 L each time), then dried with 1.0 kg of anhydrous sodium sulfate, filtered, and concentrated under reduced pressure for removing an organic solvent to obtain compound D1-5.

$^1$H NMR (400 MHz, CDCl$_3$): δ 7.49-7.33 (m, 5H), 7.03-7.00 (m, 1H), 6.90-6.86 (m, 1H), 6.76-6.74 (m, 1H), 5.47-5.45 (m, 1H), 5.11 (s, 2H), 4.49-4.44 (m, 1H), 3.90 (s, 3H), 3.06-2.95 (m, 2H), 1.39 (s, 9H).

Step 5: Preparation of Compound D1-6

Ethyl acetate (4.0 L) was added to a 10 L three-necked flask, cooled with dry ice and ethanol, charged with hydrogen chloride gas (900.0 g), then 1 L ethyl acetate was added thereto to dilute into a 4 M hydrogen chloride ethyl acetate solution. Compound A-5 (1.5 kg) was dissolved in ethyl acetate (10.0 L), 4 M solution of hydrogen chloride in ethyl acetate was added thereto to obtain a reaction solution. The reaction solution was maintained at the internal temperature not exceeding 10° C., stirred at 5-15° C. for 2 hours, then 6.0 L of isopropyl ether was added thereto, and the reaction solution was further stirred at 5-10° C. for 16 hours, then filtered to obtain a filter cake which was washed with isopropyl ether twice (1.2 L each time) to obtain compound D1-6.

$^1$H NMR (400 MHz, CD$_3$OD): δ 7.49-7.44 (m, 2H), 7.37-7.33 (m, 3H), 7.09-7.04 (m, 2H), 6.83-6.80 (m, 1H), 5.19-5.07 (m, 2H), 4.18-4.14 (m, 1H), 3.93 (s, 3H), 3.33-3.28 (m, 1H), 2.90-2.84 (m, 1H).

Step 6: Preparation of Compound D1

Compound D1-6 (2.24 kg) was evenly divided into 8 batches (302.56 g). Water (4.8 L) was added to each batch, and a solution of sodium carbonate (53.96 g) in water (302.5 mL) was added dropwise thereto to obtain a first reaction solution which was stirred for 0.5 hour and filtered to obtain a filter cake. The filter cakes of the 8 batches were combined and washed once with water (6.2 L). The resulted filter cake was added to water (22.0 L), then 85% phosphoric acid (850.0 mL) and 37% formaldehyde aqueous solution (900.0 mL) were added thereto successively to obtain a second reaction solution. The second reaction solution was stirred at 55-65° C. for 16 hours, then a solution of sodium acetate (988.7 g) in water (3.0 L) was added dropwise thereto and pH was adjusted to about 3, then the second reaction solution was filtered to obtain a filter cake which was washed four times with water (6.0 L each time) and washed once with acetone (12.0 L) and dried under vacuum to obtain Compound D1.

$^1$H NMR (400 MHz, CD$_3$OD): δ 7.49-7.30 (m, 5H), 7.02-6.93 (m, 2H), 5.04 (s, 2H), 4.30-4.20 (m, 2H), 3.89 (s, 3H), 3.74-3.70 (m, 1H), 3.54-3.48 (m, 1H), 2.92-2.84 (m, 1H).

Example 1: Preparation of a Compound Represented by Formula (I)

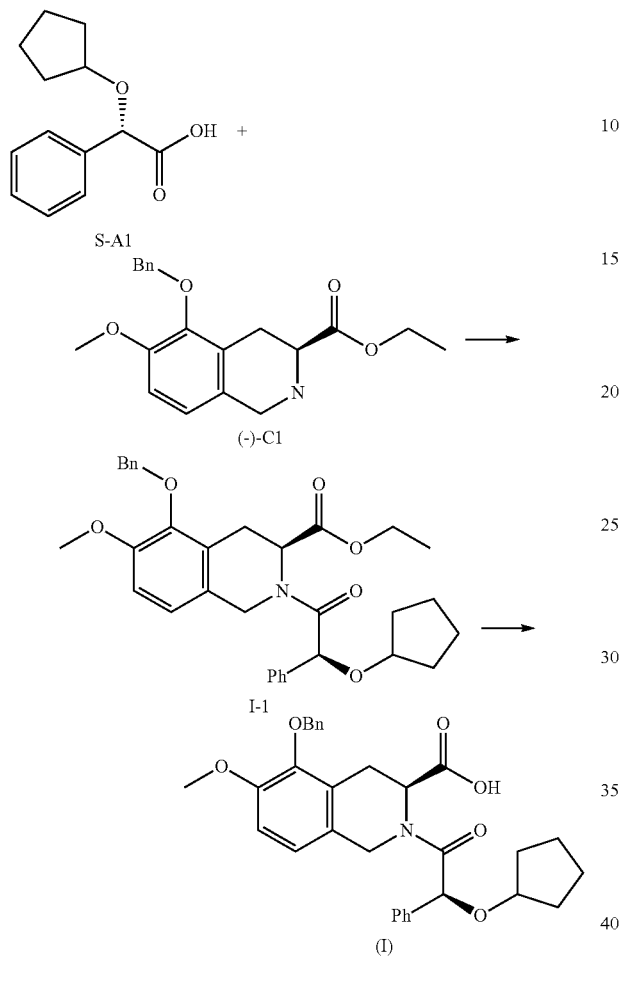

Step 1: Preparation of Compound I-1

Compound (−)-C1 (155.00 mg, 454.00 μmol) and compound S-A1 (90.00 mg, 408.60 μmol) were dissolved in dichloromethane (5.00 mL), then HATU (259.00 mg, 681.00 μmol) and diisopropylethylamine (118.00 mg, 912.54 μmol, 159.46 μL) were added thereto successively to obtain a reaction solution. The reaction solution was stirred at 20-25° C. for 16 hours and then poured into 15 mL of water, and separation is performed to obtain an aqueous phase. The aqueous phase was extracted 3 times with dichloromethane (20 mL*3), and the resulted organic phases were combined and washed once with 30 mL saturated saline solution, dried with anhydrous sodium sulfate, and dried in vacuum to obtain a crude product. The crude product was separated and purified by silica gel column chromatography (eluent: 0-50% petroleum ether/ethyl acetate) to obtain compound I-1. $^1$H NMR (400 MHz, CDCl$_3$) δ: 7.50-7.20 (m, 10H), 6.84 (m, 1H), 6.66 (d, J=8.0 Hz, 0.5H), 6.43 (d, J=12.0 Hz, 0.5H), 5.50-5.48 (m, 0.5H), 5.32 (d, J=8.0 Hz, 1H), 5.07-4.76 (m, 3H), 4.60 (d, J=16.0 Hz, 0.5H), 4.51-4.45 (m, 1H), 4.18-4.07 (m, 2H), 3.84 (d, J=12 Hz, 3H), 3.66-3.61 (m, 0.5H), 3.55-3.40 (m, 1H), 3.17-3.11 (m, 0.5H), 2.99-2.93 (m, 0.5H), 2.74-2.68 (m, 0.5H), 1.90-1.70 (m, 5H), 1.60-1.57 (m, 3H), 1.29-1.17 (m, 3H). MS m/z=544.4 [M+H]$^+$. SFC: Column: ChiralPak AD-3 (150 mm*4.6 mm, 3 μm); mobile phase: A: CO2, B: isopropanol [0.05% diethylamine]; B %: 5%-40% 5.5 min, 40% 3 min, 5% 1.5 min; Rt=5.034 min; 86.3% de.

Step 2: Preparation of Compound I

Compound I-1 (163.00 mg, 299.83 μmol) was dissolved in tetrahydrofuran (3.00 mL), and a solution of lithium hydroxide (72.00 mg, 3.01 mmol) in water (1.50 mL) was added thereto to obtain a reaction solution. The reaction solution was stirred at 15-20° C. for 48 hours, and 1M aqueous hydrochloric acid was added thereto to adjust pH to below 4, and then the reaction solution was extracted with ethyl acetate (15 mL*3) to obtain organic phases. The organic phases were combined and washed with 30 mL saturated saline solution once, dried with anhydrous sodium sulfate, and concentrated under reduced pressure to remove the organic solvents to obtain a crude product. The crude product was separated and purified by silica gel column chromatography (eluent: 0-20% dichloromethane/methanol), and the resulted product was separated again by a chiral column to obtain compound I. $^1$H NMR (400 MHz, DMSO-d6): δ 7.53-7.16 (m, 10H), 7.00-6.80 (m, 1.5H), 6.68 (d, J=8.0 Hz, 0.5H), 5.36 (d, J=12.0 Hz, 1H), 5.01-4.66 (m, 3H), 4.41 (d, J=24.0 Hz, 0.5H), 4.30 (d, J=24 Hz, 0.5H), 4.13-3.95 (m, 1H), 3.79 (s, 3H), 2.84-2.79 (m, 1H), 2.68-2.64 (m, 1H), 2.39-2.27 (m, 1H), 1.80-1.38 (m, 8H). MS m/z: 516.3 [M+1]+. SFC: Column: Chiralpak AD-3 (100 mm*4.6 mm, 3 μm); mobile phase: B: isopropanol [0.05% diethylamine]; B %: 5%-40% 4.5 min, 40% 2.5 min, 5% 1 min; Rt=4.198 min; 100.0% de.

Example 2. Preparation of Crystalline Form "A" of the Compound Represented by Formula (I)

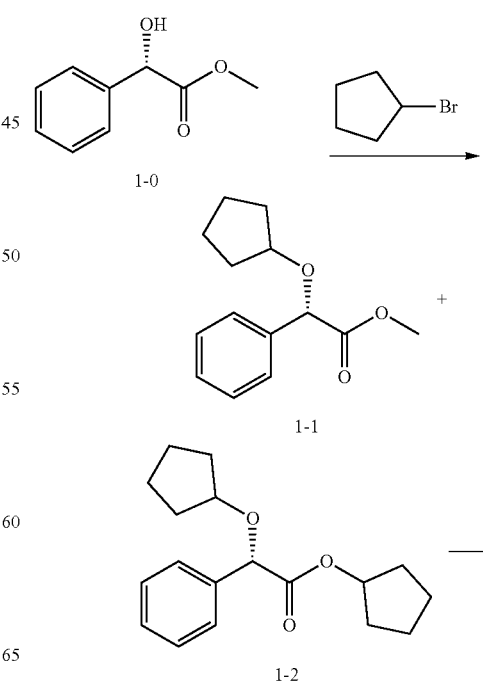

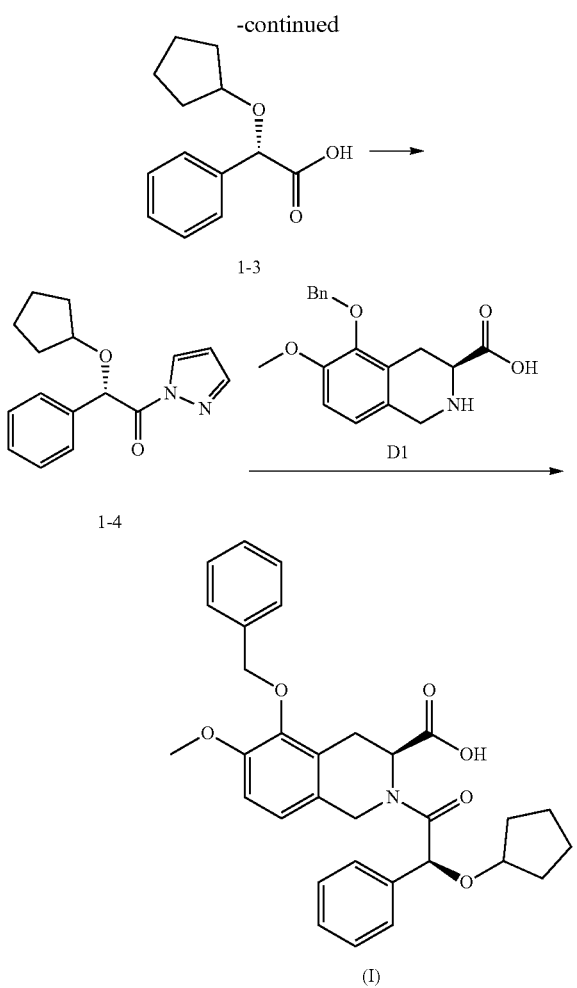

Step 1: Preparation of Compounds 1-1 and 1-2 n-heptane (8.0 L) was added to a 50 L reactor, then stirring was started, and starting materials 1-0 (1.0 kg), bromocyclopentane (3.4 kg), magnesium sulfate (1.0 kg), and silver oxide (2.0 kg) were added to the reactor to obtain a reaction solution. The reaction solution was stirred at 20-30° C. for about 19 hours, magnesium sulfate (0.3 kg) and silver oxide (0.7 kg) were added thereto, and then the reaction solution was further stirred for reaction at 20-30° C. for about 46 hours. The reaction solution was filtered under reduced pressure through silica gel (100-200 mesh, 2.0 kg) in a tabletop suction funnel to obtain a filter cake and a filtrate. The filter cake was washed with 12.0 L of dichloromethane three times, 4.0 L of dichloromethane each time to obtain a filtrate. The filtrates were transferred to a rotary evaporator, and concentrated under reduced pressure at an external temperature of 35-40° C. to obtain a mixture of compounds 1-1 and 1-2. The mixture was directly used in the next reaction without further purification.

$^1$H NMR (400 MHz, CDCl$_3$): δ 7.49-7.43 (m, 2H), 7.40-7.29 (m, 3H), 4.95 (s, 1H), 4.04-3.96 (m, 1H), 3.72 (s, 3H), 1.81-1.69 (m, 6H), 1.58-1.46 (m, 2H).

Step 2: Preparation of Compound 1-3

Tetrahydrofuran (5.3 L) was added to a 50 L reactor, then stirring was started, and the mixture (1.3 kg) of compound 1-1 and 1-2, and a solution of lithium hydroxide monohydrate (0.3 kg) in water (2.7 L) were added thereto to obtain a reaction solution. The reaction solution was stirred at 20-30° C. for 4 hours, and n-heptane (10.5 L) was added thereto, stirred for 10 minutes, and separation was performed to obtain an aqueous phase. The aqueous phase was adjusted to pH of 3-4 with 2M aqueous hydrogen chloride, and extracted twice with 16.0 L of dichloromethane, 8.0 L each time. The organic phases were combined and dried with anhydrous sodium sulfate (1.0 kg), filtered to collect a filtrate. The filtrate was concentrated under reduced pressure at an external temperature of 35-40° C. to obtain compound 1-3.

$^1$H NMR (400 MHz, CDCl$_3$): δ 7.41-7.29 (m, 5H), 4.88 (s, 1H), 4.00-3.94 (m, 1H), 1.74-1.57 (m, 6H), 1.52-1.43 (m, 2H).

Step 3: Preparation of Compound 1-4

Dichloromethane (12.0 L) was added to a 50 L reactor, and compound 1-3 (1.2 kg) was added thereto, and stirring was started. N,N-dimethylformamide (12.0 g) was added thereto, and oxalyl chloride (1.04 kg) was added dropwise thereto within 1.5 hours to obtain a reaction solution. The reaction solution was stirred at 20-30° C. for 1 hour, concentrated under reduced pressure at an external temperature of 35-40° C. to obtain a crude product which will be used in subsequent process. Dichloromethane (8.0 L) was added to a 50 L reactor, and the reactor was replaced with nitrogen twice, and stirring was started, and pyrazole (0.4 kg) and N-methylmorpholine (0.7 kg) were added thereto successively, then the temperature was cooled to 0-10° C., and the reactor was replaced with nitrogen once. The above crude product was dissolved in dichloromethane (4.0 L) to prepare a solution which was slowly dropped into the reactor. After the dropping was completed, a reaction solution was obtained and the reactor was replaced with nitrogen once. The reaction solution was heated to 20-30° C. and then stirred for about 16 hours, and then the reaction solution was successively washed twice with 10.0 L 1M sulfuric acid aqueous solution (5.0 L each time), twice with 11.0 L saturated sodium bicarbonate aqueous solution (5.5 L each time), once with 7.0 L water, and once with 8.0 L saturated sodium chloride solution. The resulted organic phase was dried with anhydrous sodium sulfate (0.5 kg), filtered to collect a filtrate which was concentrated under reduced pressure at an external temperature of 35-40° C. to obtain a crude product. The crude product was dispersed in 7.2 L n-hexane, heated to 65-75° C. and stirred for 2 hours at this temperature, then cooled to 15-25° C. and stirred for 16 hours, and filtered to collect a filter cake. The filter cake was washed twice with n-hexane (600.0 mL each time), dried under reduced pressure at an external temperature of 20-30° C. for 5 hours to obtain compound 1-4.

$^1$H NMR (400 MHz, CDCl$_3$): δ 8.24 (d, J=2.8 Hz, 1H), 7.73 (s, 1H), 7.59 (d, J=6.8 Hz, 2H), 7.41-7.27 (m, 3H), 6.43 (dd, J=1.5, 2.8 Hz, 1H), 6.36 (s, 1H), 4.21-3.98 (m, 1H), 1.87-1.67 (m, 6H), 1.57-1.43 (m, 2H).

Step 4: Preparation of Crystalline Form "A" of the Compound Represented by Formula (I)

N,N-dimethylformamide (12.0 L) was added to a 50 L reactor, and stirring was started, then compound D-1 (1220.3 g) and tetramethylguanidine (493.8 g) were added thereto successively to obtain a reaction solution. The reaction solution was stirred at 15-25° C. for 1 hour. Compound 1-4 (1211.6 g) was added to the reactor, and stirring was performed at 15-25° C. for 17 hours, then the reaction solution was poured into 12.0 L water, adjusted to pH of 3 with 2M aqueous hydrochloric acid, extracted twice with 24.0 L ethyl acetate (12.0 L each time) to obtain organic phases. The organic phases were combined and washed with 12.0 L water three times (4.0 L each time), washed once with saturated sodium chloride aqueous solution (3.0 L), dried with anhydrous sodium sulfate (500.0 g), and filtered to collect a filtrate. The filtrate was concentrated under reduced pressure at 35-40° C. to obtain a crude product. Acetone (4.0 L), water (8.0 L) and the crude product were successively added to a 50 L reactor and stirred at 35-45° C. for 20 hours, and the resulted solution was filtered to collect a filter cake. The filter cake was washed twice with 8.0 L water (4.0 L each time), dried in a vacuum drying oven at 40° C. for 21 hours to obtain a crystalline form "A" of the compound represented by formula (I).

$^1$H NMR (400 MHz, DMSO-d6): δ 12.68 (brs, 1H), 7.48-7.30 (m, 10H), 6.95-6.70 (m, 2H), 5.38-5.21 (m, 1.5H), 4.96-4.69 (m, 3.5H), 4.42-4.32 (m, 1H), 4.10-3.95 (m, 1H), 3.80 (s, 3H), 3.39-3.36 (m, 0.5H), 3.24-3.19 (m, 0.5H), 2.88-2.70 (m, 0.5H), 2.48-2.42 (m, 0.5H), 1.73-1.48 (m, 8H). LCMS (ESI) m/z: 516.0 [M+1]$^+$.

Example 3: Preparation of Crystalline Form "B" of the Compound Represented by Formula (I)

About 50 mg of the crystalline form "A" of the compound represented by formula (I) was mixed with an appropriate amount of methanol, and stirred for 2 days on a magnetic stirrer (40° C.), centrifuged to obtain a precipitate and a supernatant. Evaporative crystallization was performed with the supernatant at room temperature, and the resulted was dried overnight at room temperature in a vacuum drying oven to obtain a crystalline form "B" of the compound represented by formula (I).

About 50 mg of the crystalline form "A" of the compound represented by formula (I) was mixed with an appropriate amount of ethanol, and stirred for 2 days on a magnetic stirrer (40° C.), centrifuged to obtain a precipitate and a supernatant. Evaporative crystallization was performed with the supernatant at room temperature, and the resulted was dried overnight at room temperature in a vacuum drying oven to obtain a crystalline form "B" of the compound represented by formula (I).

About 50 mg of the crystalline form "A" of the compound represented by formula (I) was mixed with an appropriate amount of acetonitrile, and stirred for 2 days on a magnetic stirrer (40° C.), centrifuged to obtain a precipitate and a supernatant. Evaporative crystallization was performed with the supernatant at room temperature, and the resulted was dried overnight at room temperature in a vacuum drying oven to obtain a crystalline form "B" of the compound represented by formula (I).

About 50 mg of the crystalline form "A" of the compound represented by formula (I) was mixed with an appropriate amount of a mixed solvent of acetone and water at a volume ratio of 3:2, and stirred for 2 days on a magnetic stirrer (40° C.), then centrifuged to obtain a precipitate and a supernatant. Evaporative crystallization was performed with the supernatant at room temperature, and the resulted was dried overnight at room temperature in a vacuum drying oven to obtain a crystalline form "B" of the compound represented by formula (I).

$^1$H NMR (400 MHz, DMSO-d6): δ 12.68 (brs, 1H), 7.48-7.30 (m, 10H), 6.95-6.70 (m, 2H), 5.38-5.21 (m, 1.5H), 4.96-4.69 (m, 3.5H), 4.42-4.32 (m, 1H), 4.10-3.95 (m, 1H), 3.80 (s, 3H), 3.39-3.36 (m, 0.5H), 3.24-3.19 (m, 0.5H), 2.88-2.70 (m, 0.5H), 2.48-2.42 (m, 0.5H), 1.73-1.48 (m, 8H).

LCMS (ESI) m/z: 516.0 [M+1]$^+$.

Example 4: Study on the Hygroscopicity of Crystalline Form "B" of Compound Represented by Formula (I)

Experimental Materials:
SMS DVS Advantage Dynamic Vapor Sorption Intrinsic
Experimental Method:
10-15 mg of the crystalline form "B" of compound represented by formula (I) was placed in the DVS sample tray for testing.
Experimental Results:
The DVS pattern of the crystalline form "B" of compound represented by formula (I) is shown in the figure, ΔW=0.05327%.
Experimental Conclusion:
The crystalline form "B" of compound represented by formula (I) has a weight gain of 0.05327% caused by hygroscopicity at 25° C. and 80% RH, indicating it has almost no hygroscopicity.

Example 5: Solid Stability Test of Crystalline Form "B" of Compound Represented by Formula (I)

According to the "Guiding Principles for Stability Testing of Bulk Drugs and Preparations" (Chinese Pharmacopoeia 2015 Edition, Part IV, General Rule, 9001), the stability of the crystalline form "B" of compound represented by formula (I) was investigated at high temperature (60° C., open) and high humidity (room temperature/relative humidity 92.5%, open) and under light conditions (total illuminance of 1.2×10$^6$ Lux·hr/near ultraviolet 200 w·hr/m$^2$, open).

According to influencing factors and accelerated test conditions, about 5 mg of the crystalline form "B" of the compound was accurately weighed in duplicate, placed on the bottom of a 40 mL glass sample bottle, and spread into a thin layer, which was placed at high temperature (60° C.), high humidity (92.5% humidity, room temperature), high temperature and high humidity (40° C./75% humidity, 60° C./75% humidity) and light stability conditions. The open condition is formed by piercing some small holes in the aluminum foil paper to ensure that the sample can fully contact with the ambient air; and the sample placed under the strong light condition is sealed with a screw cap. The samples placed at the conditions of high temperature (60° C.) and high humidity (92.5% humidity, room temperature) were taken to test XRPD and purity on the 5th day and 10 days. Samples placed at high temperature and high humidity (40° C./75% humidity, 60° C./75% humidity) were taken to test XRPD and purity on the 10th day, 1 month, 2 months, and 3 months. The samples placed under light irradiation conditions were taken for testing when a total illuminance reached 1.2×10$^6$ Lux·hr. The test results are compared with the beginning test results of 0 day. The comparison results are shown in Table 3 below:

TABLE 3

Solid stability test results of the crystalline form "B" of the compound represented by formula (I)

| Test conditions | Test Time | Crystalline form | Purity |
| --- | --- | --- | --- |
| — | 0 day | Crystalline form "B" | 99.89% |
| High temperature (60° C., open) | 5 days | Crystalline form "B" | 99.93% |
|  | 10 days | Crystalline form "B" | 99.93% |
| High humidity (room temperature/relative humidity 92.5%, open) | 5 days | Crystalline form "B" | 99.93% |
|  | 10 days | Crystalline form "B" | 99.92% |
| Light irradiation (total illuminance of 1.2 × 10$^6$Lux · hr/near ultraviolet 200w · hr/m$^2$, open) | — | Crystalline form "B" | 99.96% |
| 40° C., relative humidity 75%, open | 10 days | Crystalline form "B" | 99.93% |
|  | 1M | Crystalline form "B" | 99.92% |
|  | 2M | Crystalline form "B" | 99.87% |
|  | 3M | Crystalline form "B" | 99.87% |
| 60° C., relative humidity 75%, open | 10 days | Crystalline form "B" | 99.92% |
|  | 1M | Crystalline form "B" | 99.90% |
|  | 2M | Crystalline form "B" | 99.78% |
|  | 3M | Crystalline form "B" | 99.80% |

Conclusion: The crystalline form "B" of the compound represented by formula (I) has good crystal stability and good chemical stability under the conditions of high temperature, high humidity, strong light and accelerated conditions.

Example 6: hAT2 Receptor Binding Assay of Compound Represented by Formula (I)

Reagents:
Solutions and Buffers
Buffers
50 mM Tris
100 mM NaCl
5 mM MgCl2
0.1% BSA
1 tablet of protease inhibitor mixture containing no ethylenediaminetetraacetic acid (Roche #11873580001) (50 mL each tablet)
pH 7.4
Experimental Methods and Steps:
1. Compound Preparation
The reference ligand PD123319 and the test compound were respectively prepared with DMSO into a 750 μM stock solution, respectively; each compound was prepared into 8 concentration gradients (the highest concentration was 750 μM, and diluted 3 times), and was added to a master plate of a 384-well plate at 10 μl/well.
SPA beads were prepared with the buffer solution into a stock solution of 25 mg/ml; Isotope [$^{125}$I]-Sar1-Ile8-Angiotensin II was added to pure water to prepare 50 uCi/ml stock solution.
2. Membrane Preparation
The cell membrane of HEK-293 cells overexpressing hAT2 was prepared into a solution of 2.5 mg/ml by the buffer.
3. Specific Operations
200 nl of compound was drawn with ECHO from the master plate to each well of the test 384-well plate. ZPE was added to an equal volume of DMSO. (The concentration of the test compound in the reaction will be diluted 250 times).
50 ml of membrane solution containing 10 μg/μl magnetic beads and 0.05 μg/μl AT2 was prepared and placed on a shaker to mix well at 100 rpm for 30 min. The test plate finally contains 1.25 μg hAT2 membrane each well and 250 μg magnetic beads each well. The membrane solution was added to the compound test plate with Multidrop Combi pipette at 25 μl each well.
50 uCi/ml isotope [$^{125}$I]-Sar1-Ile8-Angiotensin II stock solution was prepared into 0.2 nM solution with buffer, 0.2 nM 125I was added to the compound test plate with Multidrop Combi pipette at 25 μl each well. The final concentration of $^{125}$I isotope is 0.1 nM.
The configured test plate was placed on a shaker at 200 rpm and placed overnight at room temperature.
The test plate was centrifuged with a centrifuge at 1200 rpm for 1 min.
The centrifuged test plate was read with Microbeta.
Experimental Results: See Table 4.

TABLE 4

In vitro evaluation of compounds represented by formula (I)

| Compound Serial Number | hAT2 IC$_{50}$ (nM) |
| --- | --- |
| EMA-401 | 53.2 |
| (I) | 4.1 |

Conclusion: The results show that the compound represented by formula (I) has good in vitro activity compared with EMA-401.

Example 6: Determination of the Kinetic Solubility of the Compound Represented by Formula (I)

The test compound was dissolved in DMSO to prepare a stock solution of 10 mmol/L. 980 μL of dissolution medium was added with a pipette (Eppendorf Research) to a 2 mL glass tube bottle with screw cap. 20 μL of the stock solution of each test compound and the QC sample were added to the buffer solution corresponding to the kinetic detection solution at pH 7.4. The final concentrations of the test compound and DMSO solutions were 200 μM and 2%, respectively. Medicine bottle was capped. The theoretical value of the maximum concentration is 200 μM. The mixture was rotated and shaken at 880 revolutions per minute at room temperature for 24 hours, and centrifuged for 30 minutes at 13,000 revolutions per minute. 200 μL of the supernatant was added to the 96-well plate with a digital pipette. The solubility of the test compound was determined by high performance liquid chromatography spectroscopy. The experimental results are shown in Table 5.

TABLE 5

Determination of the kinetic solubility of the
compound represented by formula (I)

| Compound | Solubility (μM) @ pH = 7.4 |
|---|---|
| EMA401 | 191.7 |
| (I) | >200.0 |

Conclusion: The results show that the compound represented by formula (I) has good solubility (at pH=7.4).

Example 7: Human Liver Microsomal CYP Inhibition Experiment of Compound Represented by Formula (I)

The research project used a specific probe substrate for each isoenzyme to evaluate the inhibitory effect of the test compound on human liver microsomal cytochrome P450 isoenzymes (CYP1A2, CYP2C9, CYP2C19, CYP2D6, and CYP3A4).

Mixed human liver microsomes (pooled HLM, n≥50) were purchased from Corning Inc. (Steuben, New York, USA) or other qualified suppliers, and were stored in a refrigerator below −60° 5 before use.

The diluted series of to-be-tested compound working solutions were added to an incubation system containing cofactors of human liver microsomes, a probe substrate and a circulation system, and the methanol content was about 1% (v/v) of the final incubation system. A control containing no the to-be-tested compound and containing a solvent was used as a control for enzyme activity (100%). The concentration of the analyte in the sample was determined by liquid chromatography-tandem mass spectrometry (LC/MS/MS). The calculation was performed by using the average of the concentrations of the samples (a blank solvent, a positive control inhibitor, or the to-be-tested compound). Non-linear regression analysis was performed by using SigmaPlot (V.11) on the average percent activity of the compound to be tested to the concentration. The $IC_{50}$ value was calculated by a three-parameter or four-parameter inflection logarithmic equation. The experimental results are shown in Table 6.

TABLE 6

Human liver microsomal CYP inhibition experiment of
compound represented by formula (I)

| | Cytochrome P450 isoenzyme $IC_{50}$ (μM) | | | | |
|---|---|---|---|---|---|
| Test compound | CYP1A2 | 2C9 | 2C19 | 2D6 | 3A4 |
| EMA-401 | 13.0 | 7.28 | 17.6 | >50 | 9.19 |
| (I) | >50 | 30.5 | >50 | >50 | >50 |

Conclusion: The compound of formula (I) has no or weak inhibitory effect on the five CYP isoenzymes, indicating that there is less possibility of drug-drug interaction in the humans.

Example 8: Two-Way Permeability Study of Compound Represented by Formula (I) in CACO-2 Cells The two-way permeability of the to-be-tested compound in Caco-2 cells was measured, and whether the to-be-tested compound was transported by efflux or not was tested.

Experimental Method

Preparation of Stock Solution

The compound is dissolved in dimethyl sulfoxide (DMSO) or other suitable solvent to prepare a stock solution of the appropriate concentration.

A suitable internal standard (IS) is dissolved in acetonitrile (ACN) or other organic solvent to be used as a stop solution. The specific information will be described in the research report.

Nadolol, metoprolol, digoxin, estrone 3-sulfate potassium (E3S) and GF120918 were used as a hypotonic control compound, a hypertonic control compound, a P-glycoprotein (P-gp) substrate, a breast cancer resistance protein (BCRP) substrate, and an efflux transporter inhibitor in this study. Stock solutions of these compounds are prepared with DMSO and stored at ≤−30° C., and used within 6 months.

Preparation of Administration Solution and Receiving Solution

In this study, HBSS (Hanks Balanced Salt Solution) containing 10 mM HEPES (2-[4-(2-hydroxyethyl)-1-piperazine]ethanesulfonic acid) was used as a transport buffer (pH 7.40±0.05). The preparation method of the administration solution and the receiving solution is shown in Table 7 below.

TABLE 7

| Solution Name | Preparation method of administration solution and receiving solution | |
|---|---|---|
| | Composition | DMSO Final Concentration (v/v) |
| Administration solution | 1) to-be-tested compounds with concentrations of 2, 10 and 100 μM were prepared with a transport buffer containing or not containing 10 μM GF120918, respectively<br>2) digoxin with a concentration of 10 μM was prepared with a transport buffer containing or not containing 10 μM GF120918<br>3) E3S with a concentration of 5 μM was prepared with a transport buffer containing or not containing 10 μM GF120918<br>4) nadolol with a concentration of 2 μM and metoprolol with a concentration of 2 μM are prepared with a transport buffer containing no GF120918 | ≤0.7% |
| Receiving Solution | transport buffer containing or not containing 10 μM GF120918 | ≤0.2% |

Cell Culture

Caco-2 cells were cultured in an MEM medium (Minimum Essential Media) under the conditions of 37±1° C., 5% $CO_2$ and saturated humidity. The cells were then seeded in a Corning Transwell-96 well plate at a density of $1 \times 10^5$ cells/$cm^2$, and then the cells were placed in a carbon dioxide incubator for culture for 21-28 days for transport experiments. The medium was changed once every 5-6 days during culture.

Transport Experiment

Compounds were administered at concentrations of 2 µM, 10 µM and 100 µM and were administered in both directions (A-B and B-A directions) with or without 10 µM GF120918, and there are three parallels for each administration concentration. Digoxin and E3S were tested at the concentration of 10 µM and 5 µM, respectively, and administered bidirectionally with or without 10 µM GF120918. The test concentrations of nadolol and metoprolol were 2 µM, and nadolol and metoprolol were administered unidirectionally (the A-B direction) without 10 µM GF120918. The three control compounds were also made in three parallels.

The administration solution, receiving solution and transport buffer were pre-incubated for 30 minutes at 37° C. The cell layer was rinsed twice with the transport buffer. The administration solution and the receiving solution were separately added to the corresponding cell plate wells (75 µL and 250 µL, respectively, for each of the top and base end wells). After sampling, the cell plates were incubated for 120 minutes in an incubator at 37±1° C., 5% $CO_2$ and saturated humidity.

Sample collection information is shown in Table 8 below.

TABLE 8

| Sample collection information | | | |
|---|---|---|---|
| Sample Type | Receiving Volume Per Hole (µL) | Stop Solution Volume (µL) | Transport Buffer Volume (µL) |
| A-B Administration End | 50 | 250 | 100 |
| A-B receiving End | 150 | 250 | 0 |
| A-B Cell Lysis | 50 | 200 | 150 |
| B-A Administration End | 50 | 250 | 100 |
| B-A receiving End | 50 | 250 | 100 |
| B-A Cell Lysis | 50 | 200 | 150 |
| T0 | 50 | 250 | 100 |

After all the compounds were subjected to vortex oscillation, the compounds after vortex oscillation were centrifuged at 3220×g, and 20° C. for 20 minutes, an appropriate volume of the supernatant was transferred to a sample analysis plate, and after the plate was sealed, the compounds were stored at 2-8° C. if the compounds were not immediately analyzed. The analysis was carried out by the method of LC/MS/MS, and the specific compound treatment method is shown in the research report.

Cell Membrane Integrity Test

The Lucifer Yellow Rejection Assay was used to test the integrity of Caco-2 cells. Six cell wells were randomly selected from each cell plate, and 100 µM Lucifer Yellow was added respectively. The Lucifer Yellow Rejection Assay and the transport experiment were performed simultaneously. After 120 minutes of incubation, a Lucifer Yellow sample was taken and the relative fluorescence unit (RFU) of the Lucifer Yellow in the sample was detected at a 425/528 nm (excitation/emission) spectrum.

Sample Analysis

The concentrations of the to-be-tested compound and the control compounds nadolol, metoprolol, digoxin and E3S in the samples were determined by liquid chromatography-tandem mass spectrometry (LC/MS/MS). The retention time of the analyte and internal standard, chromatogram acquisition and chromatogram integration were processed by using the software Analyst (AB Sciex, Framingham, Mass., USA). The experimental results are shown in Table 9.

TABLE 9

| Study on two-way permeability of compound represent by formula (I) in CACO-2 cells | | | |
|---|---|---|---|
| Compound Serial Number | Papp (AB) ($10^{-6}$ cm/s) | Papp (BA) ($10^{-6}$ cm/s) | Efflux ratio |
| EMA-401 | 0.11 | 6.40 | 58.39 |
| (I) | 0.27 | 8.68 | 32.50 |

Conclusion: The test results show that the permeability of the compound of the present disclosure is improved relative to EMA-401, which is advantageous for the absorption of the compound.

The invention claimed is:

1. Crystalline form "A" of a compound represented by formula (I), wherein an X-ray powder diffraction pattern of the crystalline form "A" has characteristic diffraction peaks at the following 2θ angles: 3.52±0.20°, 6.04±0.20°, and 18.21±0.20°

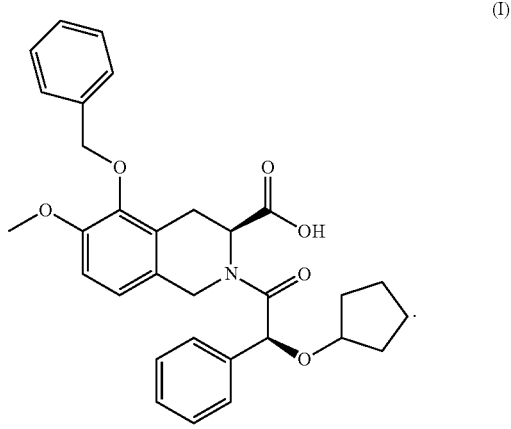 [SMILES: COc1ccc2c(c1OCc1ccccc1)C[C@@H](C(=O)O)N(C(=O)[C@@H](OC1CCCC1)c1ccccc1)C2]

(I)

2. The crystalline form "A" according to claim 1, wherein the X-ray powder diffraction pattern of the crystalline form "A" has characteristic diffraction peaks at the following 2θ angles: 3.52±0.20°, 6.04±0.20°, 14.40±0.20°, 15.11±0.20°, 18.21±0.20°, 18.46±0.20°, 20.12±0.20°, and 24.13±0.20°.

3. The crystalline form "A" according to claim 1, wherein a differential scanning calorimetry curve of the crystalline form "A" has an endothermic peak starting at 155.36° C.±3° C.

4. The crystalline form "A" according to claim 1, wherein a thermal gravimetric analysis curve of the crystalline form "A" has a weight loss of 0.1489% at 100.00° C.±3° C.

5. A method for preparing the crystalline form "A" of the compound represented by formula (I) according to claim 1, comprising steps of:

(a) dissolving the compound represented by formula (I) in a mixed solvent to obtain a first mixture;
(b) stirring the first mixture at 30–50° C. for 10-30 hours to obtain a second mixture; and
(c) filtering the second mixture to obtain a filter cake, and then drying the filter cake at 30-50° C. for 15-25 hours;
wherein, the mixed solvent is a mixture of acetone and water at a volume ratio of 1:(1.5-2.5).

6. Crystalline form "B" of a compound represented by formula (I), wherein an X-ray powder diffraction pattern of the crystalline form "B" has characteristic diffraction peaks at the following 2 θ angles: 6.08±0.20°, 12.12±0.20°, and 18.19±0.20°.

7. The crystalline form "B" according to claims. 6, wherein a differential scanning calorimetry curve of the crystalline form "B" has an endothermic peak starting at 150.95° C.±320 C.

8. The crystalline form "B" according to claims 6, wherein a thermal gravimetric analysis curve of the crystalline form "B" has a weight loss of 0.0558% at 120.00° C.±3° C.

9. A method for preparing the crystalline form "B" of the compound represented by formula (I) according to claim 6, comprising steps of:
(a) adding the compound represented by formula (I) to a solvent to obtain a first suspension;
(b) stirring the first suspension at 35-45° C. for 30-60 hours to obtain a second suspension; and
(c) centrifuging the second suspension to obtain a filter cake, and then drying the filter cake for 8-16 hours;
wherein, the solvent is selected from the group consisting of methanol, ethanol and acetonitrile; or
the solvent is a mixture of acetone and water at a volume ratio of 3:2.

10. A method for the treatment of chronic pain, comprising a step of administering the crystalline form "A" according to claim 1 to a subject in need.

11. A method for the treatment of chronic pain, comprising a step of administering the crystalline form "B" according to claim 6 to a subject in need.

12. A method for preparing a compound represented by formula (I),

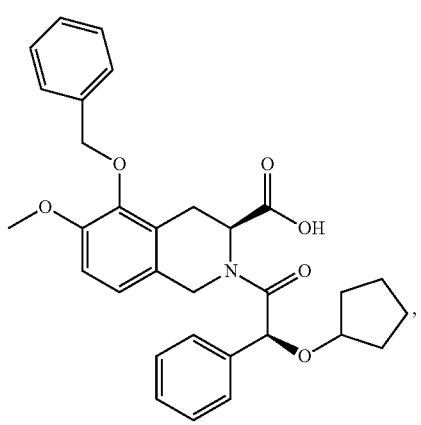

(I)

comprising steps of:

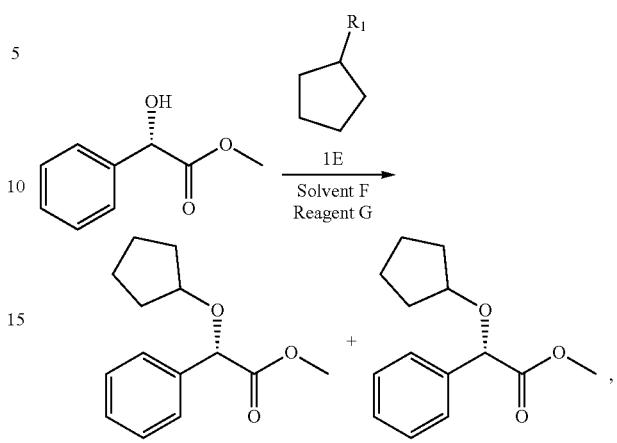

wherein,
R1 is selected from Cl, Br and I;
solvent F is selected from n-heptane, dichloromethane, tetrahydrofuran, cyclohexane and dioxane; and
reagent G is selected from silver oxide, magnesium sulfate, calcium sulfate and sodium sulfate.

13. The method according to claim 12, comprising steps of:

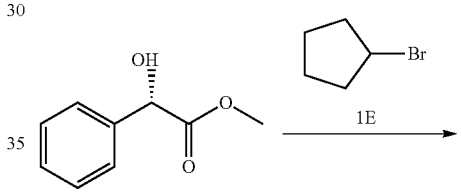

1-0

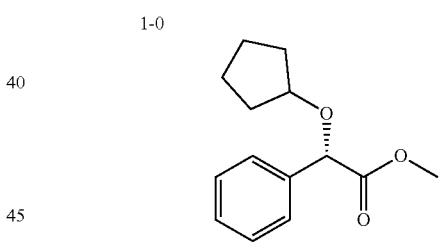

1-1

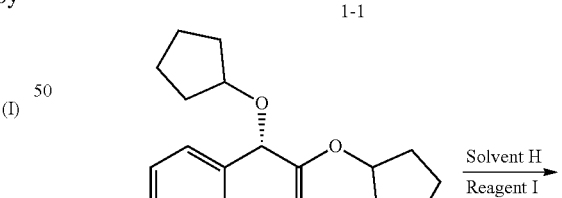

1-2

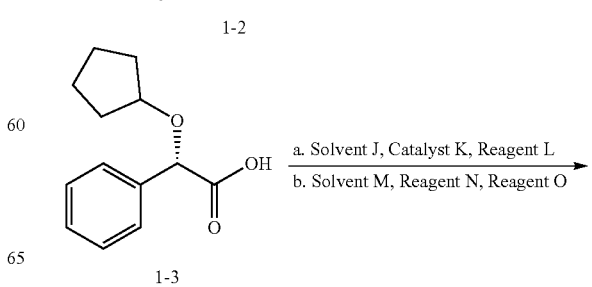

1-3

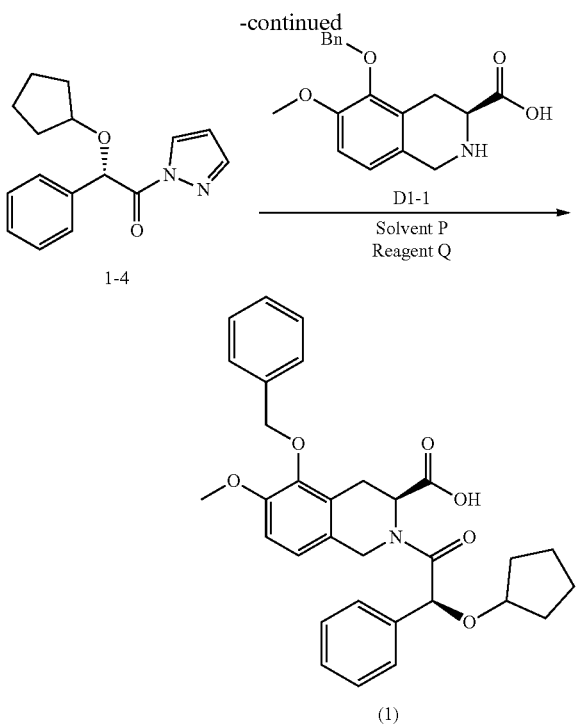

wherein,
solvent H is selected from tetrahydrofuran, methanol and water;
reagent I is selected from lithium hydroxide monohydrate and sodium hydroxide;
solvent J is selected from dichloromethane;
catalyst K is selected from N,N-dimethylformamide;
reagent L is selected from oxalyl chloride;
solvent M is selected from dichloromethane;
reagent N is selected from pyrazole;
reagent O is selected from N-methylmorpholine;
solvent P is selected from N,N-dimethylformamide, dimethyl sulfoxide, dichloromethane and tetrahydrofuran; and
reagent Q is selected from tetramethylguanidine, 1,8-diazabicycloundec-7-ene, triethylamine, diisopropylethylamine and 2,6-lutidine.

14. The method according to claim 13, wherein a molar ratio of compound 1E to compound 1-0 is (1.2-5):1.

15. The method according to claim 13, wherein a molar ratio of compound 1-4 to compound D1-1 is (1.1-1.5):1.

16. The method according to claim 13, wherein reaction systems for preparing compounds 1-1, 1-2and 1-3 are controlled at a temperature of 25±5° C.

17. The method according to claim 13, wherein preparing the compound 1-4 comprises steps a and b, wherein a reaction system in the step a is controlled to a temperature of 25±5° C.; and a reaction system in the step b is controlled to a temperature of 5±5° C. when feeding reagents into the reaction system, and the reaction system is controlled to a temperature of 25±5° C. after the reagents feeding is completed.

18. The method according to claim 13, wherein the solvent F is selected from n-heptane, a ratio of n-heptane by volume to compound 1-0 by weight being (8.0-10.0):1, and the reagent G is selected from silver oxide and magnesium sulfate, a molar ratio of silver oxide and magnesium sulfate to compound 1-0 being (1.0-5.0):1.

19. The method according to claim 12, wherein the reagent G is fed in batches.

20. The method according to claim 13, wherein the solvent H is a mixture of tetrahydrofuran and water at a volume ratio of (1-2):1, the reagent I is lithium hydroxide monohydrate, wherein a molar ratio of lithium hydroxide monohydrate to compound 1-0 is (1.0-2.0):1, a weight ratio of solvent J to compound 1-3 is 10:1, a molar ratio of catalyst K to compound 1-3 is (0.002-0.004):1, a molar ratio of reagent L to compound 1-3 is (1.2-2.0):1, a weight ratio of solvent M to compound 1-3 is (6-10):1, a molar ratio of reagent N to compound 1-3 is (1.0-1.5):1, and a molar ratio of reagent O to compound 1-3 is (1.0-1.5):1; and solvent P is selected from N,N-dimethylformamide, wherein a weiht ratio of N,N-dimethylformamide to compound 1-4 is 10:1; and the reagent Q is selected from tetramethylguanidine, wherein a molar ratio of tetramethylguanidine to compound 1-4 is (1-1.2):1.

21. The crystalline form "B" according to claim 6, wherein the X-ray powder diffraction pattern of the crystalline form "B" has characteristic diffraction peaks at the following 2θ angles: 6.08±0.20°, 12.12±0.20°, 18.19±0.20°, 24.31±0.20°, and 30.50±0.20°.

22. The crystalline form "B" according to claim 6, wherein the X-ray powder diffraction pattern of the crystalline form "B" has characteristic diffraction peaks at the following 2θ angles: 3.52±0.20°, 6.08±0.20°, 9.25±0.20°, 12.12±0.20°, 14.00±0.20°, 18.19±0.20°, 24.31±0.20°, and 30.50±0.20°.

* * * * *